United States Patent
Fraser et al.

(10) Patent No.: US 10,774,367 B2
(45) Date of Patent: Sep. 15, 2020

(54) METHODS FOR PREPARING A SAMPLE FOR NUCLEIC ACID AMPLIFICATION USING TAGMENTATION

(71) Applicant: Illumina Cambridge Limited, Nr Saffron Walden (GB)

(72) Inventors: Louise Fraser, Cambridge (GB); Paula Kokko-Gonzales, Cambridge (GB); Andrew Slatter, Cambridge (GB)

(73) Assignee: ILLUMINA CAMBRIDGE LIMITED, Nr Saffron Walden (GB)

( * ) Notice: Subject to any disclaimer, the term of this patent is extended or adjusted under 35 U.S.C. 154(b) by 19 days.

(21) Appl. No.: 16/163,005

(22) Filed: Oct. 17, 2018

(65) Prior Publication Data

US 2019/0078139 A1    Mar. 14, 2019

Related U.S. Application Data

(63) Continuation of application No. 14/733,452, filed on Jun. 8, 2015, now abandoned.

(60) Provisional application No. 62/171,814, filed on Jun. 5, 2015, provisional application No. 62/171,908, filed on Jun. 5, 2015.

(30) Foreign Application Priority Data

Jun. 9, 2014   (GB) .................................. 1410196.8
Jul. 9, 2014   (GB) .................................. 1412207.1

(51) Int. Cl.
    C12P 19/34    (2006.01)
    C12Q 1/6806   (2018.01)
    C12N 15/10    (2006.01)
    C12Q 1/6844   (2018.01)

(52) U.S. Cl.
    CPC ....... *C12Q 1/6806* (2013.01); *C12N 15/1003* (2013.01); *C12P 19/34* (2013.01); *C12Q 1/6846* (2013.01)

(58) Field of Classification Search
    None
    See application file for complete search history.

(56) References Cited

U.S. PATENT DOCUMENTS

| | | | |
|---|---|---|---|
| 8,728,764 B2 | 5/2014 | Boutell | |
| 10,017,759 B2* | 7/2018 | Kaper | C12N 15/1093 |
| 2008/0242555 A1 | 10/2008 | Shen et al. | |
| 2009/0042290 A1 | 2/2009 | Steele et al. | |
| 2012/0122737 A1 | 5/2012 | Sabot et al. | |
| 2013/0065223 A1 | 3/2013 | Klein et al. | |
| 2015/0087534 A1* | 3/2015 | Gormley | C12Q 1/6806 506/4 |
| 2015/0337298 A1* | 11/2015 | Xi | C12Q 1/6806 506/16 |
| 2018/0104690 A1* | 4/2018 | Blainey | F04B 19/006 |

FOREIGN PATENT DOCUMENTS

| | | |
|---|---|---|
| CN | 102344919 | 2/2012 |
| EP | 2388312 | 11/2011 |
| WO | WO 2009/016652 | 2/2009 |
| WO | WO 2010/038042 | 4/2010 |
| WO | WO 2011/025477 | 3/2011 |
| WO | WO 2012/034030 | 3/2012 |
| WO | WO 2013/131962 | 9/2013 |
| WO | WO 2015/189588 | 12/2015 |
| WO | WO 2017/006108 | 1/2017 |

OTHER PUBLICATIONS

Adey et al., Genome Biology 11:R119, 1-17 (2010). (Year: 2010).*
Agilent Technologies, SureDirect Blood PCR Kit: Protocol, 2014.
April et al., Whole-Genome Gene Expression Profiling of Formalin-Fixed Paraffin-Embedded Tissue Samples, PLOS One 2009, 4(12), e8162.
Chacon-Cortes, Diego et al., "Comparison of genomic DNA,'K.R. H/ extraction techniques from whole blood samples: a time, cost and quality evaluation study", Molecular Biology Reports; An International Journal on Molecular and Cellular Biology (vol. 39. No. 5), Jan. 7, 2012, 5961-5966.
Fedick et al., High-throughput real-time PCR-based genotyping without DNA purification, BMS Research Notes, Biomed Central Ltd., GB, 2012, 5(1), 573.
Goldenberger, D. et al., "Technical A Simple "Universal" DNA Extraction Procedure Using SOS and Proteinase K Is Compatible with Direct PCR Amplification", Genome Res, 1995, 4, 368-370.
Herraez-Hernandez et al., Detection and Genotyping of Human Papillomavirus DNA in Formalin-Fixed Paraffin-Embedded Specimens with the HPV Direct Flow Chip System, Open Virol J, 2013, 7, 91-95.
Kanai, et al., "Rapid and simple method for preparation of genomic DNA from easily obtainable clotted blood", Journal of Clinical Pathology, vol. 47, No. 11, Nov. 1, 1994, 1043-1044.
Park et al., Detection of Hepatitis C Virus RNA Using Ligation-Dependent Polymerase Chain Reaction in Formalin-Fixed, Paraffin-Embedded Liver Tissues, Am. J. Pathol. 1996, 149(5), 1485-1491.
Park et al., Direct STR Amplification from Whole Blood and Blood—or Saliva-Spotted FTA without DNA Purification, J. Forensic Sci. 2008, 53(2), 335-341.
Zhang et al., Direct DNA Amplification of Crude Clinical Samples Using a PCR Enhancer Cocktail and Novel Mutants of Taq, J. Molecular Diagnostics 2010, 12(2), 153-154.
International Search Report and Written Opinion for Application No. PCT/GB2015/051674, dated Jul. 30, 2015.

* cited by examiner

*Primary Examiner* — Kenneth R Horlick
(74) *Attorney, Agent, or Firm* — Knobbe, Martens, Olson & Bear LLP

(57) ABSTRACT

Presented are methods and compositions for preparing samples for amplification and sequencing. Particular embodiments relate to methods of preparing nucleic acid-containing cellular samples for library amplification, wherein the methods include providing nucleic acid containing-cellular samples from blood or FFPE samples, lysing cells of the sample to liberate nucleic acids, and performing tagmentation without purifying the liberated nucleic acids.

20 Claims, 27 Drawing Sheets

| Metric | QiaAmp | QuickExtract |
|---|---|---|
| Predilution required | 1/10 | 1/2 |
| Density (K/mm2) | 159 | 305 |
| Clusters PF | 1.26M | 2.43M |
| Clusters PF (%) | 91.3 | 97.0 |
| % >= Q30 | 97.3 | 98.7 |
| Align to human (%) | 96.6 | 97.9 |
| on target (%) | 97.6 | 97.8 |
| Amplicon uniformity 0.2 (%) | 80.1 | 88.2 |

| Density | 12x1 K/mm2 |
|---|---|
| Passing Filters | 83.7% |
| Aligned | 99.5% |
| > Q30 | 95.6% |
| Uniformity | 94% |

- 140623_HSQ1098_0350_BC48NPACXX

Lane Results Summary : Read 1

Workflow

| Lane Info | | | | Tile Mean ± SD for Lane | | | | | |
|---|---|---|---|---|---|---|---|---|---|
| Lane | Lane Yield (kbases) | Clusters (raw) | Clusters (PF) | 1st Cycle Int (PF) | % Intensity after 20 cycles (PF) | % PF Clusters | % Align (PF) | Alignment Score (PF) | % Mismatch Rate (PF) |
| 1 | 17823728 | 935528 ± 47915 | 919128 ± 57008 | 1368.8 ± 132.3 | 87.2 ± 1.8 | 96.15 ± 2.17 | 96.36 ± 0.05 | 55.34 ± 0.03 | 0.38 ± 0.02 |
| 2 | 27021992 | 1491999 ± 69050 | 1393461 ± 121213 | 1172.0 ± 136.3 | 87.1 ± 2.5 | 93.24 ± 4.70 | 96.33 ± 0.05 | 55.16 ± 0.04 | 0.39 ± 0.02 |
| 3 | 17995611 | 915359 ± 64754 | 881581 ± 71192 | 1170.9 ± 131.7 | 87.0 ± 1.7 | 96.26 ± 2.23 | 96.25 ± 0.06 | 54.86 ± 0.04 | 0.39 ± 0.02 |
| 4 | 26648568 | 1464366 ± 60243 | 1374204 ± 97940 | 1139.6 ± 127.5 | 86.6 ± 1.8 | 93.75 ± 3.69 | 96.24 ± 0.06 | 54.83 ± 0.05 | 0.40 ± 0.05 |
| 5 | 23768640 | 1173096 ± 48258 | 1122507 ± 64279 | 1243.3 ± 139.9 | 85.6 ± 1.2 | 95.64 ± 2.32 | 96.12 ± 0.06 | 54.89 ± 0.03 | 0.39 ± 0.01 |
| 6 | 33913782 | 1730373 ± 70646 | 1640563 ± 112405 | 1236.5 ± 123.0 | 85.3 ± 1.5 | 93.21 ± 3.23 | 96.09 ± 0.05 | 54.83 ± 0.04 | 0.40 ± 0.03 |
| 7 | 19114184 | 1020064 ± 63210 | 965674 ± 64585 | 1186.4 ± 112.4 | 86.1 ± 1.6 | 96.61 ± 1.24 | 96.16 ± 0.05 | 54.82 ± 0.04 | 0.40 ± 0.01 |
| 8 | 28152027 | 1580134 ± 102089 | 1451735 ± 204056 | 1157.6 ± 134.8 | 87.1 ± 4.8 | 91.39 ± 2.71 | 96.14 ± 0.05 | 54.83 ± 0.08 | 0.41 ± 0.02 |

Lanes 1, 2, 3, 4 indicated on right.

Nextera tagmentation based whole genome sequencing directly from blood spots on HiSeq

Figure 15

| Diversity | Depth | GC d.o. | AT d.o |
|---|---|---|---|
| 4.11 billion | 4.8 x | 0.31 | 3.23 |

| Diversity | Depth | GC d.o. | AT d.o |
|---|---|---|---|
| 2.25 billion | 0.16 x | 0.03 | 7.85 |

| Prep | Truseq (gDNA) | Nextera (gDNA) | 2ul Blood Nextera | Blood BBN 1 Pre-Assembled, SPRI | Blood BBN 2 On-bead, Zymo | Blood BBN 3 On-bead, SPRI | Direct blood spot | Indirect blood spot |
|---|---|---|---|---|---|---|---|---|
| read length | 2x100 | 2x100 | 2x100 | 2x100 | 2x100 | 2x100 | 2x100 | 2x100 |
| mean raw density (K/mm2) | 817 | 821 | 854 | 925 | 961 | 724 | 808 | 980 |
| mean %PF | 88.1 | 95.0 | 95.3 | 94.3 | 92.5 | 95.1 | 88.0 | 93.4 |
| mean %align (PF) | 90.0 | 96.1 | 95.6 | 96.7 | 95.1 | 97.3 | 95.3 | 95.7 |
| mean %>Q30 | 95.2 | 95.8 | 96.2 | 95.5 | 90.4 | 91.5 | 86.5 | 94.9 |
| Coverage before downsampling | 35.7 | 35.6 | 34.1 | 38.4 | 36.8 | 31.9 | 36.0 | 32.7 |
| Downsampled coverage | 29.9 | 30.0 | 30.1 | 30.2 | 30.1 | 29.8 | 30.8 | 30.2 |

Columns grouped as: gDNA controls (Truseq, Nextera); EDTA Blood (2ul Blood Nextera, Blood BBN 1, Blood BBN 2, Blood BBN 3); Blood Spots (Direct blood spot, Indirect blood spot).

Figure 19

| Coverage Uniformity | Horizon cell line | Colon tumour 1 | Colon tumour 2 |
|---|---|---|---|
| Qiagen purification (2h 45min) | 94% | 80% | 69% |
| 1h 20min workflow | 88% | 88% | 60% |
| 1h 2min workflow | 96% | - | 62% |
| 2 min workflow | 91% | - | 65% |

Figure 26

METHODS FOR PREPARING A SAMPLE FOR NUCLEIC ACID AMPLIFICATION USING TAGMENTATION

FIELD

The present invention relates to methods for preparing samples for subsequent nucleic acid (e.g. DNA) amplification, which methods are simpler to perform than existing methods. In particular, the present invention relates to methods wherein purifying nucleic acid (e.g. DNA) from a sample is not required prior to amplification.

BACKGROUND

Traditional DNA amplification methods typically require purified DNA to be obtained prior to the amplification steps. The purification process typically requires enzymatic digestion or lysis of cells in a cellular sample, followed by one or more separation steps to separate out the DNA from the cellular debris, which may include one or more washing steps and final elution of the purified DNA into a tube ready for use in an amplification process (such as PCR). The process often takes upwards of 30 minutes, typically 40 minutes or more.

Recently, Sigma has developed a so-called 'Extract-N-Amp™ Blood PCR Kit', which contains reagents necessary to extract host genomic DNA from whole blood and amplify targets of interest by PCR. This extraction system reduces the need for purification, organic extraction, centrifugation, heating, filtration or alcohol precipitation. The kit also includes a PCR Ready mix, especially formulated for amplification directly from the extract. This formulation uses an antibody based Hot Start, for specific amplification. Genomic DNA is extracted from 10 µl of whole blood by simply adding the Extraction Solution (which appears to be potassium hydroxide) and incubating for 5 minutes at room temperature. The Neutralization Solution is added to the extract to counteract inhibitory substances prior to PCR. A portion of the DNA extract is then added to the specially formulated PCR mix.

It is an object of the present invention to provide sample preparation methods that do not require purification of DNA prior to amplification. Preferably, those methods require only simple reagents, which reduces the time and cost burden on persons performing the preparations.

SUMMARY

In one embodiment of the present invention, there is provided a method of preparing a sample for library amplification and subsequent amplification comprising the following steps:
(a) providing a nucleic acid-containing cellular sample;
(b) lysing cells of the sample to liberate nucleic acid from within the cells of the cellular sample, thereby forming a lysate; and
(c) amplifying the nucleic acid from the lysed samples;
wherein there is no purification of the nucleic acid from the lysed sample prior to beginning the amplification step (c).
Preferably the nucleic acid is DNA.
Preferably the sample is a clinical or non-clinical sample.
Preferably the sample is a blood sample.
Preferably the blood sample is a whole blood sample.
In one embodiment, the sample is taken from a culture. In another embodiment, the sample is taken from a microbiological culture (e.g., a blood culture).
Preferably the sample is a non-blood sample, such as a tissue sample (e.g. tumor, biopsy), an aspirate, etc.
Preferably the lysis reagent is water, preferably purified/distilled water.
Preferably the lysis reagent not water. Examples may include detergents, acids, bases, enzymes.
Preferably the sample and lysis reagent are mixed together to achieve more even distribution.
Optionally an enzyme is further added to the lysate in order to disrupt the DNA structure. Preferably the enzyme is proteinase K.
Optionally, there is a neutralizing step after lysis of the cells with the lysis reagent to inactivate the lysis reagent if required. Preferably this neutralizing step is prior to the amplification step (c). In some aspects, the neutralizing step can be considered as part of an incubation period. The same or an additional neutralizing step can also be performed in order to neutralize any other agent in the lysate that may interfere with subsequent amplification steps, such as proteinase K when tagmentation is to be performed as part of the amplification process.
Optionally there is an incubation period after combining the sample and the lysis reagent. The incubation period should be sufficient to allow lysis of a portion, preferably the majority or substantially all or all, of the cells in the sample, including their cell membranes (and preferably including nuclear membranes), such that nucleic acid (e.g. DNA) of the cell becomes accessible for suitable amplification. Whilst incubation can occur at temperatures higher than room temperature, incubation does not necessarily imply that a raised temperature is used. Incubation can occur at or around room temperature, or at less than room temperature. Times for incubation can range from a couple of seconds, e.g. about 5, 10, 15, 20, 25, 30, 35, 40, 45, 50, 55, 60 seconds, to a number of minutes, e.g. about 1, 1.5, 2, 2.5, 3, 3.5, 4, 4.5, 5, 5.5, 6, 6, 5, 7, 7.5, 8, 8.5, 9, 9.5, 10 minutes. Longer incubation periods may be required depending on the sample and/or lysis reagent, such as about 20, 30, 40, 50, 60, 70, 80, 90 minutes. Ranges of incubation times are also permitted, involving a combination of any of the above-mentioned times as being lower and upper limits, respectively (e.g. about 0.5-10 minutes, about 1-5 minutes, about 2-5 minutes, about 1-8 minutes, etc.).
In one aspect of the present invention, the steps of lysing the sample and amplifying the nucleic acid contained therein is conducted in a single pot reaction.
The lysate formed from lysing the cells can comprise all of the contents and fragments of cell membranes etc. produced when the cell is lysed, such as e.g. the cytoplasm and its components. In the context of the present invention, the lysate may also be considered as being the contents of the lysed cell excluding such things as cell membrane fragments and larger cellular debris (such as organelles etc. (that e.g. have escaped lysis during the lysis step)). In other words, the lysate may comprise the cytosol of the cell, along with lipids, proteins, and nucleic acids.
By the term "there is no purification of the nucleic acid from the lysed sample prior to beginning the amplification step (c)" it is meant that the nucleic acid (e.g. DNA) is not isolated or separated away from the lysate prior to initiating the amplification process (the amplification process itself may of course comprise steps of purifying the nucleic acid as part of the amplification process). However, it is not meant to limit additional steps being performed to alter or modify the nucleic acid (e.g. DNA) or its tertiary structure after lysis and before amplification in order that the amplification process can be carried out successfully.

In one aspect of the invention, quantification of the amount of DNA in the lysate is conducted prior to the amplification step.

In further embodiments of the present invention, the amplified DNA is sequenced to ascertain its sequence. This can be done by any method known in the art. Preferably, it is sequenced by high throughput sequencing, such as a sequence by synthesis protocol.

BRIEF DESCRIPTION OF THE DRAWINGS

FIG. 4 shows a data table of the sequencing metrics for the targeted DNA amplification assay of FIGS. 3A and 3B;

FIG. 15 (a data table of sequencing metrics) shows the results of the sequencing of FIG. 14.

FIG. 19 shows a data table of sequencing metrics for three BBN samples (BBN1, 2, 3) as compared to sequencing metrics of purified gDNA controls.

FIG. 26 is a data table comparing coverage uniformity obtained for sequencing libraries obtained using 4 different workflows from 3 different FFPE samples.

DETAILED DESCRIPTION

The invention provides methods of preparing samples for nucleic acid amplification. The nucleic acid may be DNA, or RNA. In one embodiment, the invention provides methods of preparing a blood sample for nucleic acid amplification, preferably wherein the blood sample is a whole blood sample.

In another embodiment, the invention provides methods of preparing non-blood samples, such as tissue samples (e.g. formalin fixed paraffin-embedded (FFPE) samples) for DNA amplification. Such tissue samples may be tumor samples. Other samples may be biopsies, or aspirates, etc.

DNA amplification may be performed according to the methods described in the WO2010/038042 publication, the WO2011/025477 publication, PCT application PCT/US2014/071263, filed Dec. 18, 2014, and/or PCT application PCT/EP2014/079145, filed Dec. 23, 2014, each of which is incorporated herein by reference in its entirety. Targeted DNA amplification may be used to enrich target sequences for subsequent cluster generation and sequencing.

The methods of the invention preferably use (whole) blood or non-blood (e.g. FFPE) tissue samples as sample input. The methods of the invention obviate the need for nucleic acid (e.g. DNA) purification prior to amplification.

The invention also provides a method for tagmentation (e.g. using the Nextera™ process (Illumina, Inc.)) of nucleic acid (e.g. DNA) in a sample, such as a whole blood sample.

In simple terms, the present invention provides the steps of:
(a) providing a nucleic acid-containing cellular sample;
(b) lysing cells of the sample to liberate nucleic acid from within the cells of the cellular sample, thereby forming a lysate; and
(c) amplifying the nucleic acid from the lysed samples; wherein there is no purification of the nucleic acid from the lysed sample prior to beginning the amplification step (c).

Figure 1:
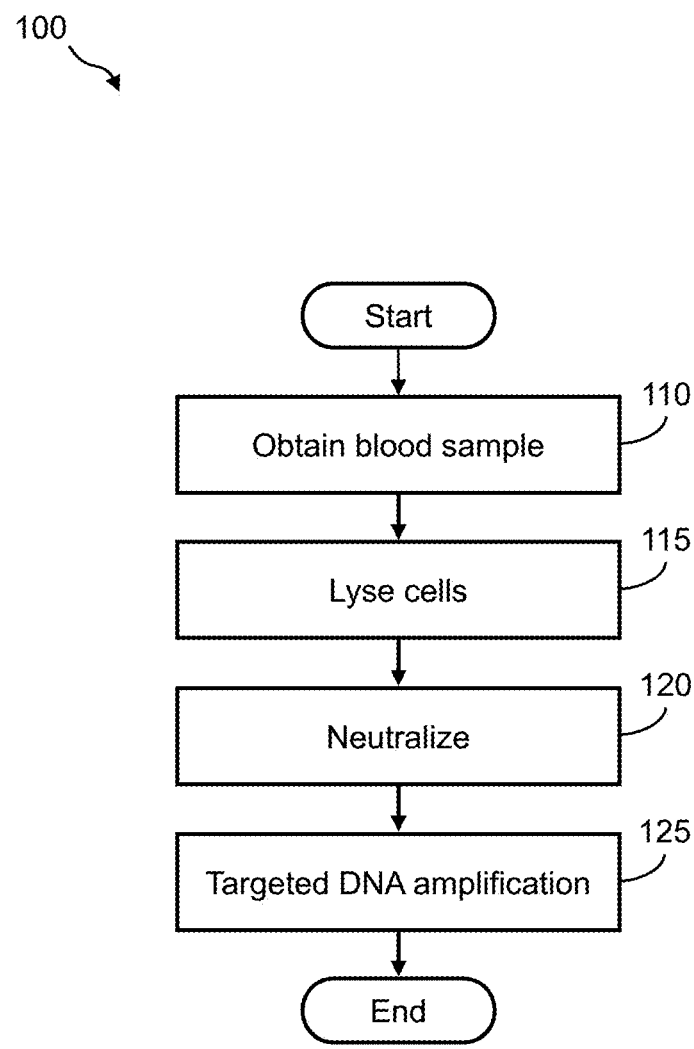
FIG. 1 illustrates a flow diagram of an example of method of preparing a whole blood sample for targeted DNA amplification.

FIG. 1 illustrates a flow diagram of an example of method 100 of preparing a whole blood sample for targeted DNA amplification. For example, targeted DNA amplification may be performed according to the methods described in the WO2010/038042 publication, the WO2011/025477 publication, PCT application PCT/US2014/071263, filed Dec. 18, 2014, and/or PCT application PCT/EP2014/079145, filed Dec. 23, 2014, each of which is incorporated herein by reference in its entirety. Method 100 includes, but is not limited to, the following steps.

At a step 110, a nucleic acid-containing sample is obtained or provided. This can be a blood sample, or a non-blood sample such as a tissue sample, biopsy, aspirate, etc. An example of a tissue sample might be e.g. a tumor sample. If the sample is a blood sample, then preferably it is a whole blood sample.

The quantity of sample provided will depend on the sample and on the subsequent procedure that will be conducted on the sample. Typically, sample amounts for liquid samples may be in the region of approx. 1, 2, 3, 4, 5, 6, 7, 8, 9, 10, 11, 12, 13, 14, 15, 20 µL. Such amounts are suitable for blood samples which will undergo a PCR amplification process. In some aspects, the blood sample amount will be approx. 10 µL. In other aspects, the blood sample amount will be approx. 2 µL.

In embodiments of the present invention where a solid sample is provided, a sufficient amount of sample should be used which will liberate sufficient nucleic acid. The skilled person will be aware of how to prepare a suitable amount of sample.

At a step 115, the cells in the sample (e.g. whole blood, tissue) are lysed. For example, an aliquot (e.g. 10 µL) of the whole blood sample is mixed with an amount of a lysis reagent. The lysis reagent may be any suitable reagent for disrupting and/or solubilizing the cell membrane.

A lysis solution is one that is capable of lysing cells (e.g., by solubilizing eukaryotic cell membranes). Preferably, the lysis solution is one that leaves nucleic acid intact (i.e. that does not denature a nucleic acid chain to an extent that the chain is disrupted to individual nucleic acids). In one embodiment, the lysis solution can comprise one or more detergents, one or more enzymes, or a combination of one or more detergents and one or more enzymes, and can further include additional agents. In one embodiment, the detergent can be a non-denaturing lytic detergent, such as Triton® X-100 Triton® X-100-R, Triton® X-114, NP-40, Genapol® C-100, Genapol® X-100, Igepal® CA 630, Arlasolve™ 200, Brij® 96/97, CHAPS, octyl β-D-glucopyranoside, saponin, and nonaethylene glycol monododecyl ether (C12E9, polidocenol). Optionally, solubilizers can also be included, such as Brij® 98, Brij® 58, Brij® 35, Tween® 80, Tween® 20, Pluronic® L64, Pluronic® P84, non-detergent sulfobetaines (NDSB 201), amphipols (PMAL-C8), and methyl-β-cyclodextrin. Typically, non-denaturing detergents and solubilizers are used at concentrations above their critical micelle concentration (CMC), while denaturing detergents may be added at concentrations below their CMC. For example, non-denaturing lytic detergents can be used at a concentration of about 0.010% to about 10%, e.g., about 0.015% to about 1.0%, e.g., about 0.05% to about 0.5%, e.g., about 0.10% to about 0.30% (final concentration after dilution with the sample). In another embodiment, polyoxyethylene detergent detergents may be preferred. The polyoxyethylene detergent can comprise the structure $C_{12-18}/E_{9-10}$, wherein C12-18 denotes a carbon chain length of from 12 to 18 carbon atoms and E9-10 denotes from 9 to 10 oxyethylene hydrophilic head groups. For example, the polyoxyethylene detergent can be selected from the group consisting of Brij® 97, Brij® 96V, Genapol® C-100, Genapol® X-100, nonaethylene glycol monododecyl ether (polidocanol), or a combination thereof.

Enzymes that can be used in lysis solutions include, without limitation, enzymes that are considered membrane-fouling materials (e.g., proteinase XXIII, neuraminidase, polysaccharidase, Glucanex®, and Pectinex®). Other additives that can be used include, without limitation, reducing agents such as 2-mercaptoethanol (2-Me) or dithiothreitol (DTT) and stabilizing agents such as magnesium, pyruvate, and humectants.

The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS.

In one example, the lysis reagent is the lysis reagent from an "Extract-N-Amp" Blood PCR kit (available from Sigma).

A suitable volume of a lysis reagent is e.g. 10 µL to 200 µL, depending on the reagent. Volumes might be selected from approx. 10, 20, 30, 40, 50, 60, 70, 80, 90, 100 µL, and will depend on the amount of sample to be lysed.

In one embodiment, a lysis reagent (e.g. lysis reagent from an "Extract-N-Amp" Blood PCR kit (available from Sigma), e.g. potassium hydroxide, might be used at approx. 20 µL, when 10 µL of e.g. blood is used.

Preferably the lysis reagent is water, preferably distilled water. In one embodiment, water is used preferably in an amount of 90 µL, where a 10 µL sample e.g. blood is provided. The skilled person will be able to vary the amount of water used dependent on the sample size in accordance with their general knowledge and usual lab practices. For example, a volume of 12 µL water may be mixed with a 2 µL aliquot of whole blood.

After the lysis reagent (e.g. water) has been added to the cell sample (e.g. blood sample), the mixture may optionally be mixed (e.g. via a vortex mixer, or by shaking by hand). Mixing allows the lysis reagent and sample to be evenly distributed, so that the sample is lysed as equally as possible. Mixing may occur for a few to a number of seconds (e.g. 5 s to 60 s).

It should be appreciated that the lysis reagent may be added to the sample, or the sample may be added to the lysis reagent.

After the lysis reagent and sample have been combined and optionally mixed, there is an incubation period. This allows the lysis reagent sufficient time to lyse the cells in the sample. The optional mixing step may also form part of the time of the incubation period.

In one embodiment, the sample and the lysis solution are mixed and then incubated for a sufficient time for lysis and solubilization of cell membranes to occur, e.g., about 1, 2, 3, 4, 5, 10, 15, 20, 25, 30, 40, 50, or 60 seconds, or about 2, 3, 4, 5, 6, 7, 8, 9, 10, 15, or 20 minutes or longer, e.g., about 1 second to about 20 minutes, about 1 second to about 5 minutes, or about 1 second to about 2 minutes. Longer incubation times may also be necessary depending on the sample and/or lysis reagent. For example, approx. 30, 40, 50, 60, 70, 80, 90 minutes. The incubation time will depend on the strength of the lysis solution, e.g., the concentration of the detergent and/or enzymes. The lysis can take place at a temperature of about 2° C. to about 45° C., e.g., about 15° C. to about 40° C., e.g., about 30° C. to about 40° C., room temperature, etc. In one embodiment, the lysis solution can be loaded into a syringe and the sample can then be aspirated into the syringe such that mixing and incubation occurs within the syringe. In one embodiment, the lysis solution can be loaded into a syringe and the sample can then be aspirated into the syringe such that mixing and incubation occurs within the syringe.

In an embodiment of the present invention, particularly where the lysis reagent is not water, the incubation time is approx. 5 mins at room temperature.

In a particularly preferred embodiment of the invention where the lysis reagent is water (i.e. without any other lysis reagent (e.g. detergent)), the incubation time (room temp) is approx. 2 mins. This represents a significant time saving over using non-water detergent lysis reagents.

At a step 120, there is an optional neutralization step. This may be needed if the lysis reagent is required to be neutralized prior to the amplification step, due to interference of the lysis reagent with the amplification process that would otherwise occur.

In preferred embodiments of the present invention, the lysis reagent is selected such that no neutralizing step is required. The use of water as a lysis reagent does not require a subsequent neutralizing step prior to amplification.

Where a neutralizing step is required, the skilled person will be well aware of the amount of neutralizing agent required to neutralize the lysis reagent. For example, the lysis reaction can be neutralized by the addition of a neutralization reagent from the "Extract-N-Amp" Blood PCR kit. A suitable amount of such a reagent may be approx. 180 μL.

At a step 125, an aliquot of the lysed (and optionally neutralized) blood sample is amplified by targeted DNA amplification. Any suitable amplification method may be used, and will typically employ PCR. The present invention is not necessarily limited by a particular amplification process. Depending on the type of amplification method employed, the amount of lysed sample required for the amplification process will vary accordingly. For example, an amount of 1, 2, 3, 4, 5, 6, 7, 8, 9, 10, 11, 12, 13, 14, 15, 16, 17, 18, 19, 20 μL may be suitable for the amplification process. For example, 2, or 4 μL.

Nucleic Acid Amplification and Clustering

In some embodiments, the immobilized DNA fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein.

For example one or more clusters or colonies can be formed via solid-phase PCR whether one or both primers of each pair of amplification primers are immobilized.

In other embodiments, the immobilized DNA fragments are amplified in solution. For example, in some embodiments, the immobilized DNA fragments are cleaved or otherwise liberated from the solid support and amplification primers are then hybridized in solution to the liberated molecules. In other embodiments, amplification primers are hybridized to the immobilized DNA fragments for one or more initial amplification steps, followed by subsequent amplification steps in solution. Thus, in some embodiments an immobilized nucleic acid template can be used to produce solution-phase amplicons.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the Golden-Gate assay (Illumina, Inc., San Diego, Calif.) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

As can be seen in the present invention, the time savings using the simplified method of nucleic acid preparation (e.g. approx. 2-5 mins) where no DNA purification is conducted over traditional DNA purification techniques (e.g. over 20 mins, typically 30-120 mins) is significant.

Figure 2:
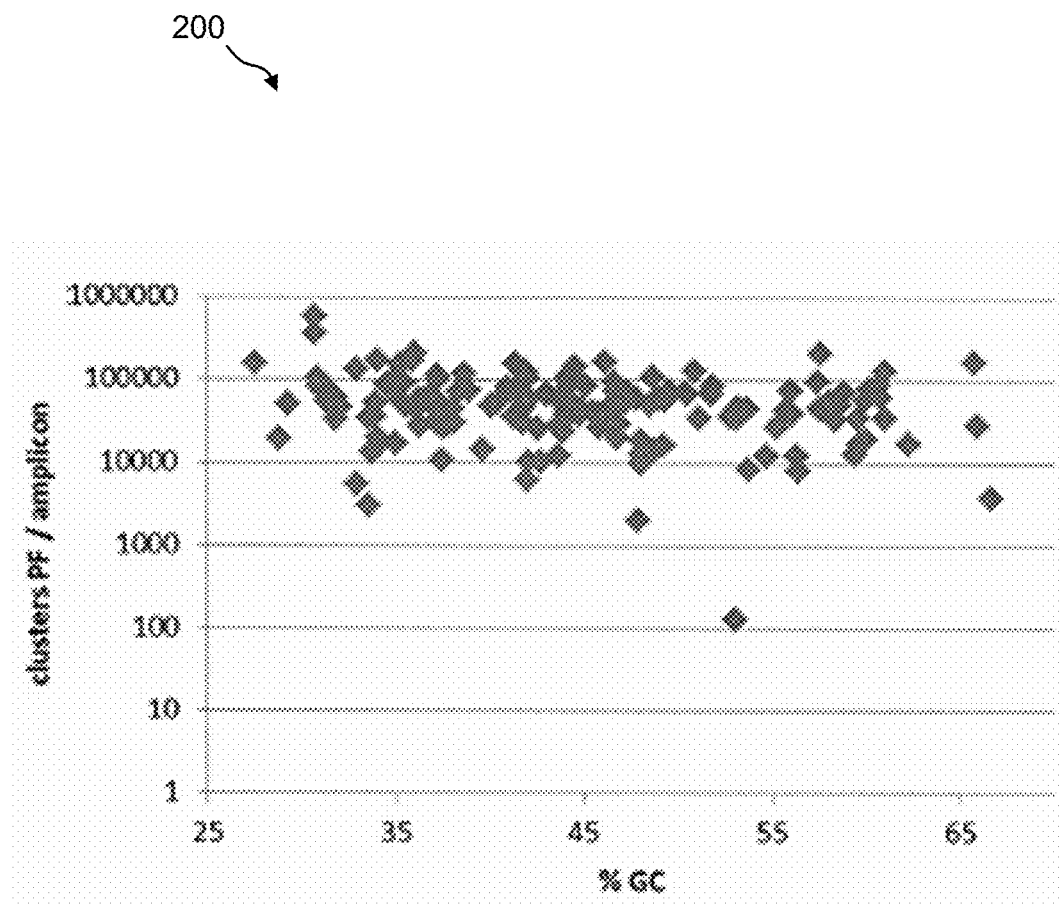
FIG. 2 shows a plot of clusters that pass filter for amplicons generated by targeted DNA amplification of a whole blood sample prepared according to the method of FIG. 1.

FIG. 2 shows a plot 200 of clusters that pass filter for amplicons generated by targeted DNA amplification of a whole blood sample prepared according to method 100 of FIG. 1. In particular, 10 µL whole blood, 20 µL lysis reagent ("Extract-N-Amp" Blood PCR kit, Sigma), 5 min incubation at room temp, 180 µL neutralizing reagent ("Extract-N-Amp" Blood PCR kit, Sigma), 4 µL lysate to PCR. When clusters are analyzed, the least reliable data (often derived from overlapping clusters) is removed from the analysis results. Therefore, the raw data is filtered to remove any reads that do not meet the overall quality as measured by a chastity filter. The chastity of a base call is calculated as the ratio of the brightest intensity divided by the sum of the brightest and second brightest intensities. For example, clusters "pass filter (PF)" if no more than one base call in the first 25 cycles has a chastity of <0.6. When sequencing reads are aligned to the reference genome, for example the human genome, the first 32 bases of the read are matched to a position in the human genome and an alignment is made so long as there are no more than 2 mismatches within the 32 base seed. Reads that could be aligned in more than one position in the genome are still classified as aligning, but they align with a low alignment score. Bases are scored for quality based on a combination of metrics, including their chastity score, whether they follow a known difficult sequence and where they fall in the sequencing read. For example, the percent of bases with a Q score of 30 or more can be reported which means that there is a probability of 1 in 1000 that this base call is incorrect. The coverage metric reported indicates the number of times a particular region of the genome has been covered by sequencing reads. The diversity metric reported is an estimated number of unique fragments present in the original sequencing library. AT and GC drop out metrics refer to the difference in the AT or GC content in the reads versus the reference.

In this experiment, an aliquot of the DNA amplification product was loaded onto a flow cell with capture probes for clonal amplification (cluster generation) and sequencing (MiSeq). Each point on plot 200 represents an amplicon and shows the percent GC content of the amplicon as a function of clusters per amplicon. In the targeted amplification assay, for example, a uniformity value can be quoted. This metric reports the percentage of amplicons that are covered within 0.2× mean coverage, i.e., it would not include amplicons sequenced at a frequency of less than 20% of the mean coverage of all the amplicons. The sequencing metrics are shown in Table 1. The data show that all amplicons are covered. In this sequencing example, the cluster density is 1626,000 clusters per mm$^2$ of flow cell surface, 80.54% of the clusters pass filters, 99.4% of the passing filters clusters align to the human genome and 94.7% of the passing filters clusters have a quality of greater or equal to Q30.

TABLE 1

| MiSeq metrics | |
| --- | --- |
| Density | 1626 K/mm$^2$ |
| PF | 80.54% |
| Align | 99.4% |
| >=Q30 | 94.7% |

Figure 3A:
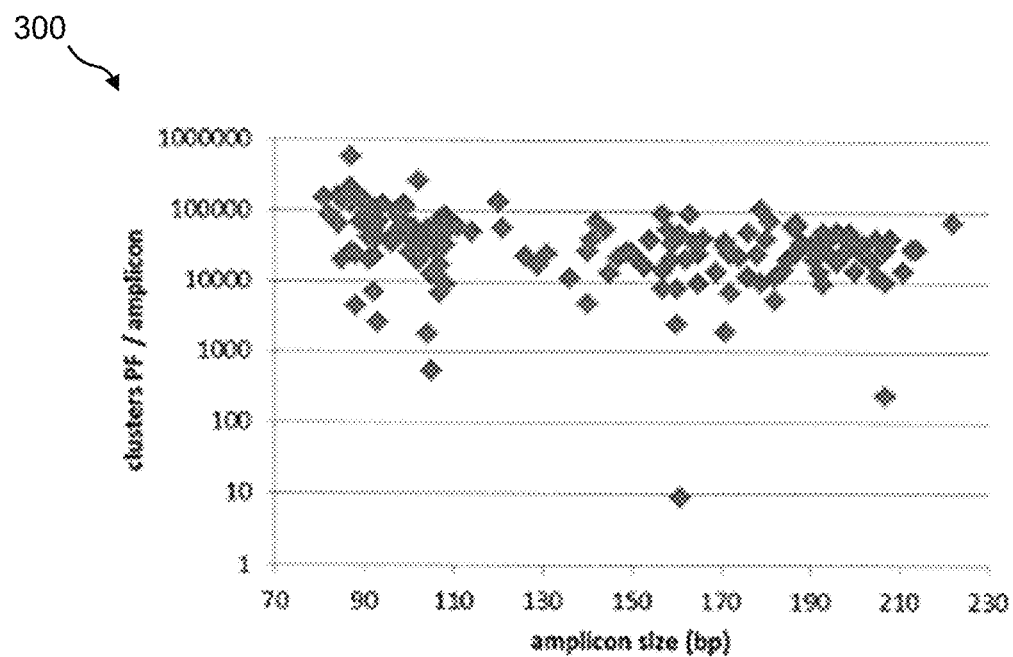
FIGS. 3A and 3B show a plot of amplicon size and a plot of percent GC content, respectively, from a targeted DNA amplification assay performed on a whole blood sample prepared by dilution with water.
Figure 3B:
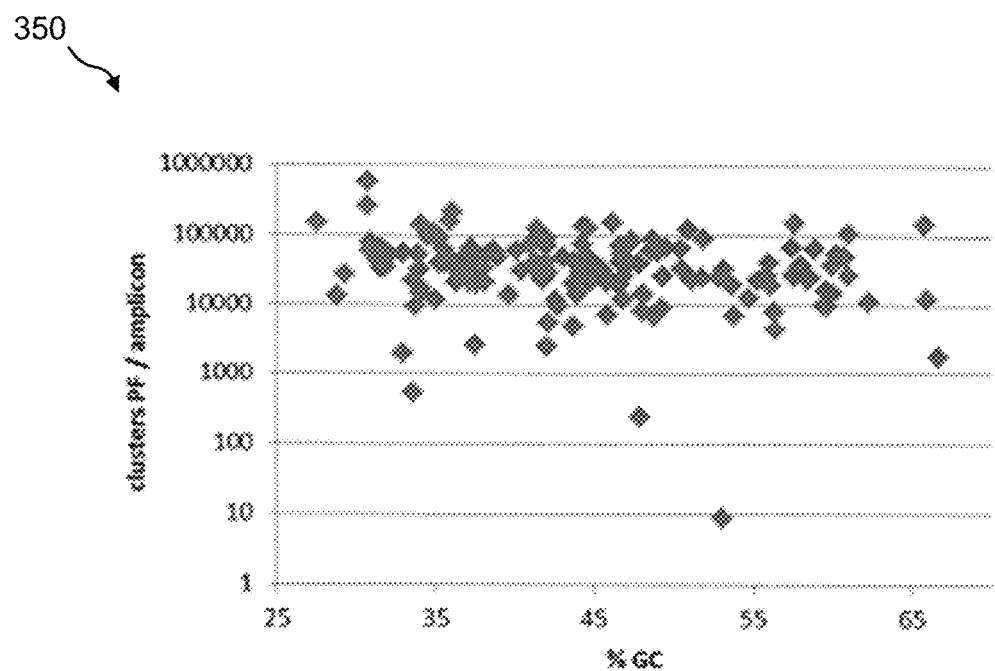

FIGS. 3A and 3B show the results from a simplified method of preparing a whole blood sample for targeted DNA amplification, where an aliquot (10 µL) of a whole blood sample is mixed with water (90 µL) prior to amplification (2 µL lysate used for PCR amplification process, same process as for FIG. 2). For example, targeted DNA amplification may be performed according to the methods described in the WO2010/038042 publication, the WO2011/025477 publication, PCT application PCT/US2014/071263, filed Dec. 18, 2014, and/or PCT application PCT/EP2014/079145, filed Dec. 23, 2014, each of which is incorporated herein by reference in its entirety. Here, the incubation time was only approx. 2 mins, which effectively was the time taken to mix the blood sample and water together and then prepare the amplification step.

FIGS. 3A and 3B show a plot 300 of amplicon size and a plot 350 of percent GC content, respectively, from a targeted DNA amplification assay performed on a whole blood sample prepared by dilution with water. In this example, 10 µL of a whole blood sample was mixed with 90 µL of water. In this sample preparation protocol, water is acting as a lysing agent. A 2 µL aliquot of the sample (lysate) was amplified by targeted DNA amplification. An aliquot of the DNA amplification product was loaded onto a flow cell with capture probes for clonal amplification (cluster generation) and sequencing (MiSeq). Each point on plots 300 and 350 represent an amplicon.

These results show that the DNA preparation with water alone as the lysis reagent gives comparable results as the DNA preparation using a non-water lysis reagent (e.g. lysis reagent from "Extract-N-Amp" Blood PCR kit, Sigma).

Figure 4:
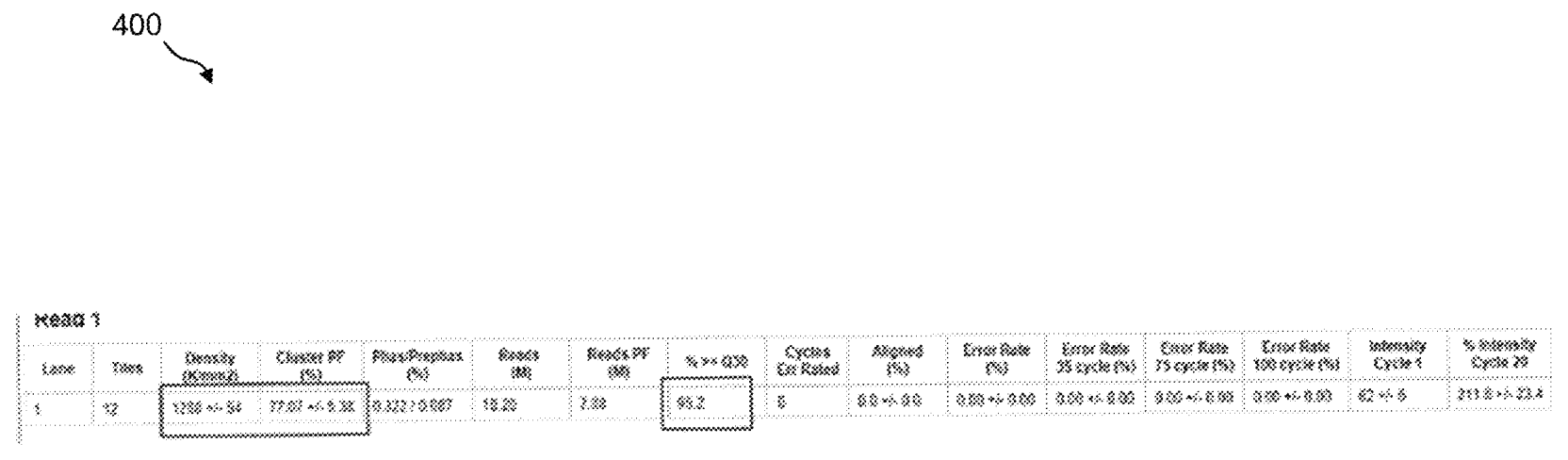

FIG. 4 shows a data table 400 of the sequencing metrics for the targeted DNA amplification assay of FIGS. 3A and 3B. The data of FIGS. 3A, 3B, and 4 show that dilution of whole blood sample in water is sufficient for preparing a blood sample for targeted DNA amplification and subsequent cluster generation and sequencing.

In yet another embodiment of the invention, a whole blood sample is used directly for targeted DNA amplification. For example, targeted DNA amplification may be performed according to the methods described in the WO2010/038042 publication, the WO2011/025477 publication, the U.S. PCT application PCT/US2014/071263, filed Dec. 18, 2014, and/or PCT application PCT/EP2014/079145, filed Dec. 23, 2014, each of which is incorporated herein by reference in its entirety.

In this embodiment, an enzyme is used to lyse the cells (e.g. blood cells) directly, as part of the amplification process.

A particularly preferred enzyme is Phusion DNA polymerase (New England Biolabs, Thermo Scientific®), a High-Fidelity DNA Polymerase. High-Fidelity DNA Polymerases are important for applications in which the DNA sequence needs to be correct after amplification. Phusion High-Fidelity DNA Polymerase offers both high fidelity and robust performance, and thus can be used for all PCR applications. Its structure, a novel *Pyrococcus*-like enzyme fused with a processivity-enhancing domain, increases fidelity and speed. Phusion DNA Polymerase is using for cloning and can be used for long or difficult amplicons. With an error rate supposedly of >50-fold lower than that of Taq DNA Polymerase and 6-fold lower than that of *Pyrococcus furiosus* DNA Polymerase, Phusion is allegedly one of the most accurate thermostable polymerases available. Phusion DNA Polymerase possesses 5'→3' polymerase activity, 3'→5' exonuclease activity and will generate blunt-ended products.

Figure 5:
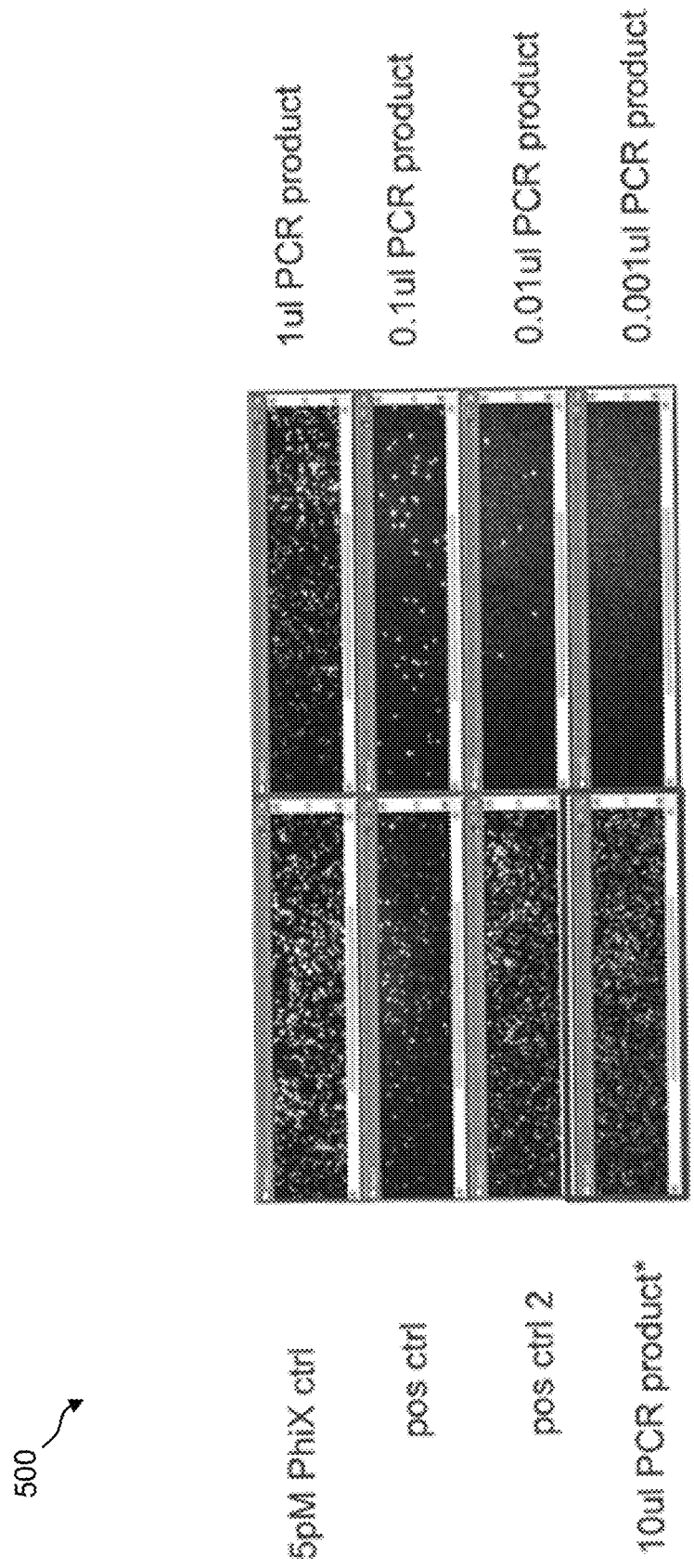
FIG. 5 shows panels of clusters generated from amplicons generated directly from a whole blood sample by targeted DNA amplification.

FIG. 5 shows panels of clusters generated from amplicons generated directly from a whole blood sample by targeted DNA amplification. In this example, 2 µL of whole blood is mixed directly with 48 µL of PCR mix containing Phusion enzyme (50 µL reaction volume). Cluster generation was performed using 10, 1, 0.1, 0.01, and 0.001 µL of amplified PCR products. PhiX (5 pM), and target sequences positive controls were used as positive controls.

Figure 6:
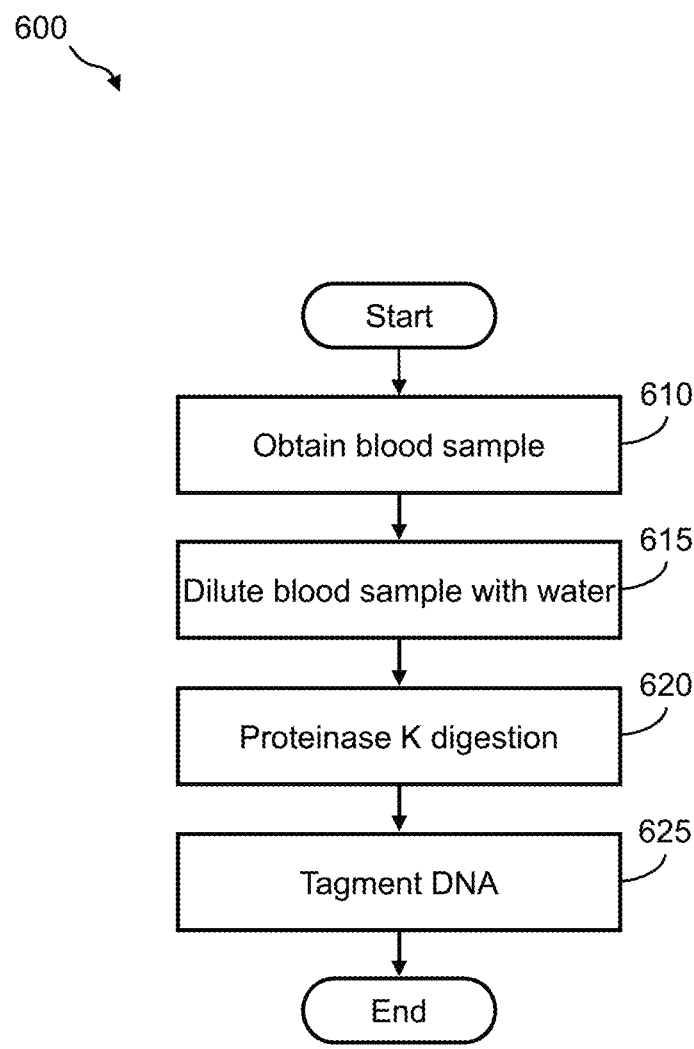
FIG. 6 illustrates a flow diagram of an example of a method of preparing a whole blood sample for construction of a tagmented DNA library (Nextera)

FIG. 6 illustrates a flow diagram of another aspect of the present invention, in this case a method 600 of preparing a sample (e.g. whole blood) for construction of a tagmented DNA library (e.g. via Nextera™, Illumina, Inc.). Method 600 includes, but is not limited to, the following steps.

At a step 610, a sample (e.g. whole blood) is obtained or provided.

At a step 615, an aliquot (e.g. 2 µL) of whole blood is mixed with water (e.g. 12 µL).

At a step 620, as a specific step when the amplification process involves tagmentation, proteinase K is added to the blood sample to disrupt the chromatin. If proteinase K is not added, then the DNA does not fully unfold (i.e. is remains associated with histones) and larger sequences of DNA ultimately become tagmented. In one example, 1 µL of proteinase K is added to the 14 µL blood+water sample and incubated at approx. 56° C. for 20 minutes. The proteinase K is subsequently inactivated by heating the sample at 70° C. for 10 minutes.

This reaction is advantageously performed as a single pot reaction, again not requiring any purification of the DNA prior to the tagmentation steps.

At a step 625, the sample is tagmented using a modified Nextera reaction to generate a tagmented DNA library. In one example, a tagmentation protocol is based on a fast lysis protocol, Nextera kit #1502811, and an indexed kit #15028216. Briefly, 25 µL tagment DNA buffer (TD) and 10 µL tagment DNA enzyme (TDE1) are added to a fast lysis sample and incubated for 5 minutes at 55° C. The sample is then cooled on ice. The sample is purified using a Zymo purification column and eluted to 25 µL. A 20 µL aliquot of the purified sample is PCR amplified using 5 µL of both index primers (e.g., indexes N702 and N507), 15 µL Nextera PCR mastermix (NPM), and 5 µL PCR primer cocktail (PPC). Thermal amplification is performed according to manufacturer's recommendation. The sample volume is adjusted (if necessary) to 30 µL with resuspension buffer (RSB) and purified using SPRI beads.

The purified library is eluted from the SPRI beads with 32.5 µL RSB. The fragment size distribution in the library and DNA concentration are determined.

Figure 7A:
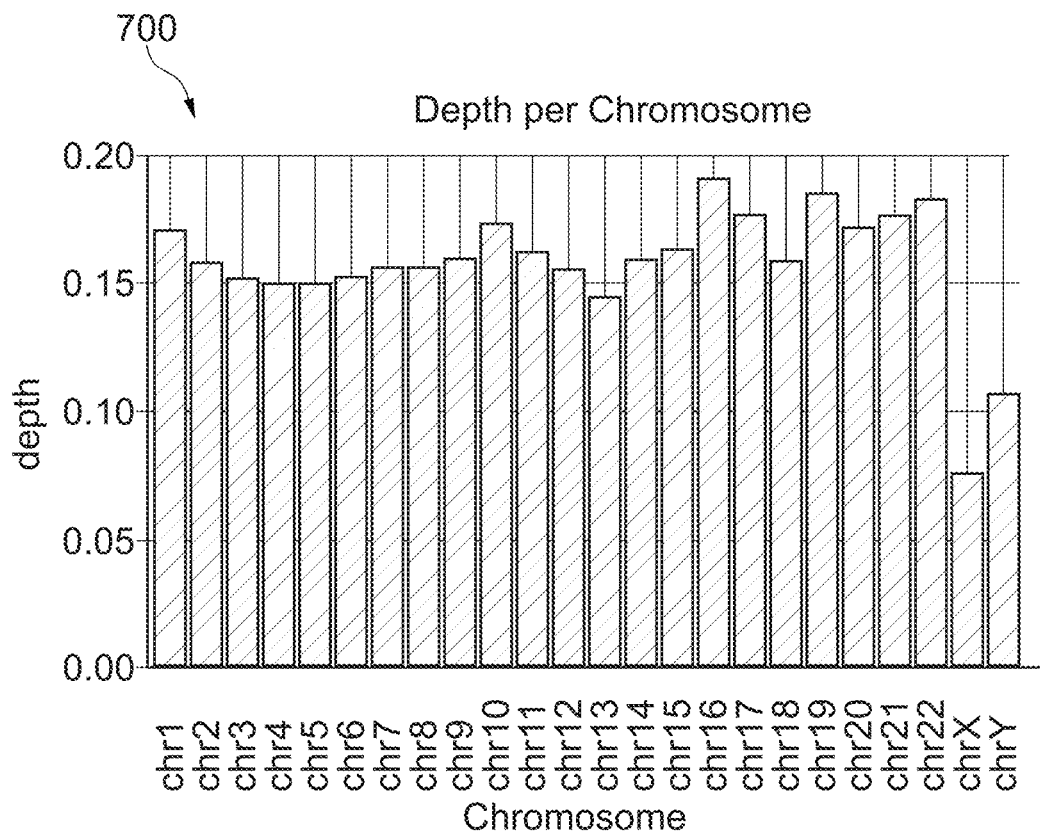
FIGS. 7A and 7B show a bar graph of sequencing depth per chromosome and a plot of the size distribution, respectively, of a tagmented DNA library prepared according to the method of FIG. 6.
Figure 7B:
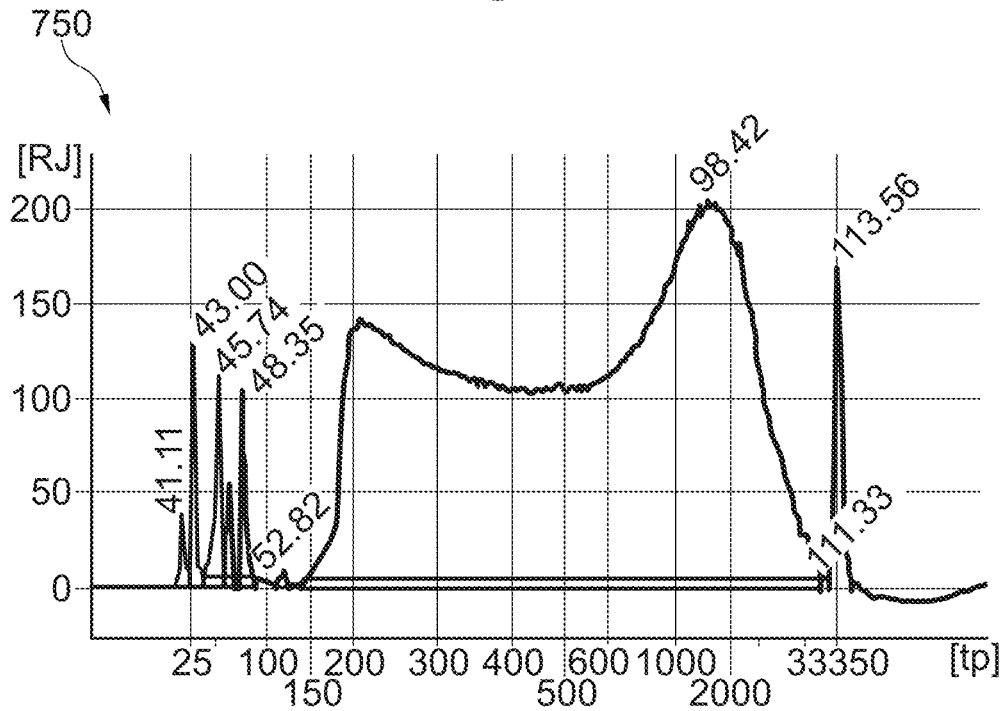

FIGS. 7A and 7B show a bar graph 700 of sequencing depth per chromosome and a plot 750 of the size distribution, respectively, of a tagmented DNA library prepared according to method 600 of FIG. 6. An aliquot of the tagmented DNA library was loaded onto a flow cell for clonal amplification (cluster generation) and sequencing (MiSeq). The sequencing metrics are shown in Table 2. In this sequencing example, the cluster density is 424,000 clusters per $mm^2$ of flow cell surface, 96.65% of the clusters pass filters, 93.45% of the passing filters clusters align to the human genome, and 98.2% of the passing filters clusters have a quality of greater or equal to Q30. The library diversity is 4.63 billion and the depth of coverage of the human genome is 0.15×. GC and AT drop out is 0.35 and 16.31 respectively.

TABLE 2

| MiSeq metrics | |
| --- | --- |
| Density | 424 K/$mm^2$ |
| PF | 96.65% |
| Align | 93.45% |
| >=Q30 | 98.2% |
| Div | 4.63 billion |
| Depth | 0.15x |
| GD d.o. | 0.35 |
| AT d.o. | 16.31 |

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

The method of the invention can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

In standard sample preparation methods, each template contains an adaptor at either end of the insert and often a number of steps are required to both modify the DNA or RNA and to purify the desired products of the modification reactions. These steps are performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wis.).

More examples of transposition systems that can be used with certain embodiments provided herein include Staphylococcus aureus Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol. Methods 71:332-5).

Sequencing Directly from FFPE

Also presented herein are methods for preparing a sequencing library directly from an FFPE sample. In some embodiments, the method comprises amplification of nucleic acid from the FFPE sample without performing a xylene deparafinization step. In some embodiments, the method comprises amplification of nucleic acid from the FFPE sample without performing a separate extraction step. In some embodiments, amplification is performed directly in a vessel comprising the FFPE sample.

Figure 8:
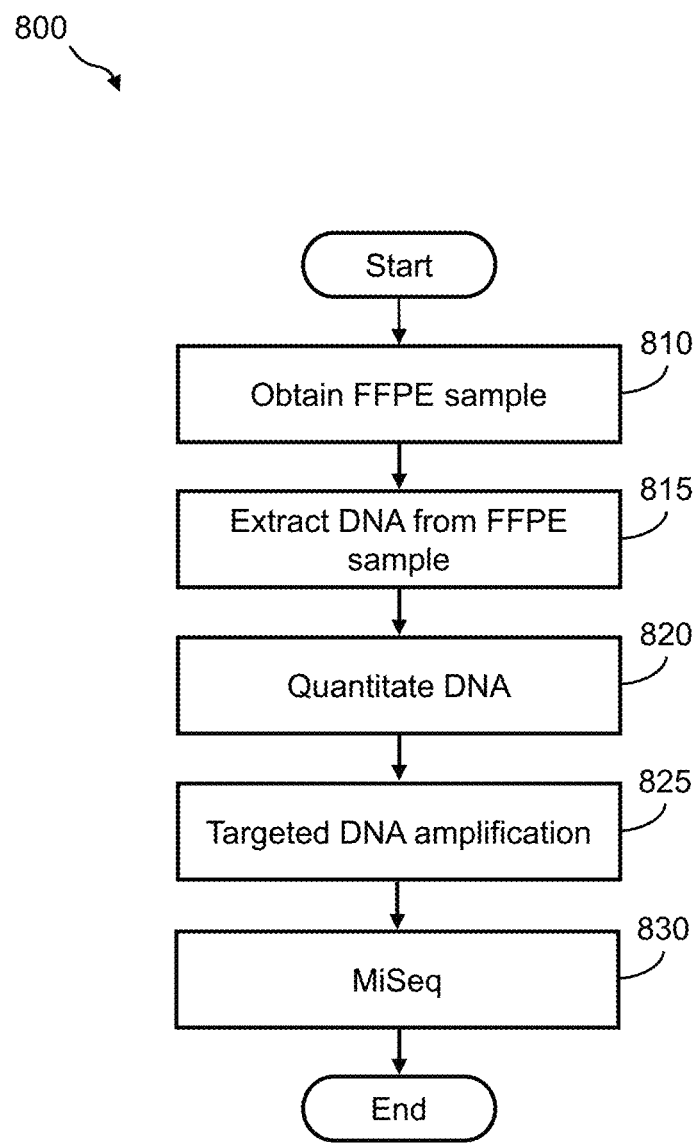
FIG. 8 illustrates a flow diagram of an example of a method of preparing an FFPE sample for targeted amplification and subsequent sequencing.

FIG. 8 illustrates a flow diagram of an example of a method 800 of preparing a tissue sample (e.g. FFPE sample) for targeted DNA amplification and subsequent sequencing. Targeted DNA amplification may, for example, be performed according to the methods described in the WO2010/038042 publication, the WO2011/025477 publication, PCT application PCT/US2014/071263, filed Dec. 18, 2014, and/ or PCT application PCT/EP2014/079145, filed Dec. 23, 2014, each of which is incorporated herein by reference in its entirety. Method 800 includes, but is not limited to, the following steps.

At a step 810, a tissue sample (e.g. slice of an FFPE sample) is obtained. In one example the FFPE sample is a paraffin-embedded cell culture sample. In another example, the FFPE sample is a tumor sample or a normal tissue sample.

At a step 815, DNA from the sample is extracted. In one example, the QuickExtract buffer (available from EpiCentre) is used to extract DNA from the FFPE sample. In this example, 100 µL of QuickExtract buffer is added to the FFPE sample in a microfuge tube, the tube is vortexed, and incubated for 1 hour at 56° C., followed by a 2 minute incubation at 98° C.

At a step 820, the DNA in the sample is quantitated. There are several methods known to the skilled person to quantitate the average concentration of DNA present in the mixture, including spectrophotometric quantification and UV fluorescence in the presence of a dye.

At a step 825, targeted DNA amplification is performed on the extracted DNA sample. In one example, targeted DNA amplification is performed using 10 ng of extracted DNA.

Preferably, by 'extracted DNA' it is meant the DNA that has become accessible through lysis of the cellular sample. Thus, 10 ng of extracted DNA may actually require a larger volume of lysate to be provided.

At a step 830, the amplified DNA is diluted (e.g., ½₀) and loaded onto a flow cell prepared with capture probes for cluster generation and sequencing (MiSeq).

In one example, method 800 of FIG. 8 is used to prepare a colon tumor FFPE sample for targeted amplification.

Figure 9A:
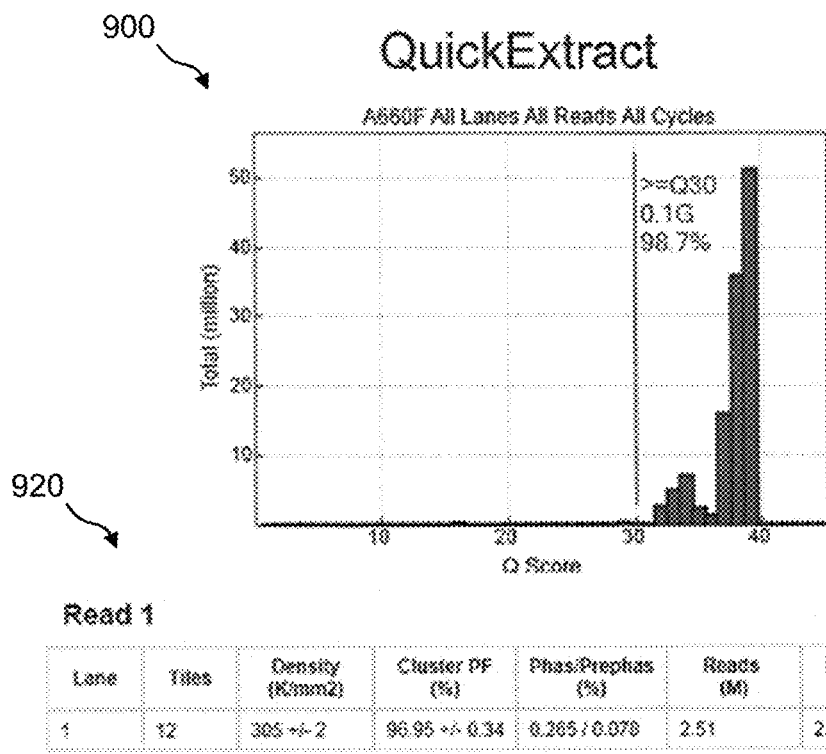
FIG. 9A shows a bar graph of the Q score metric and a data table of sequencing metrics for amplicons generated from DNA prepared from a colon tumor FFPE sample according to the method of FIG. 8.
Figure 9B:
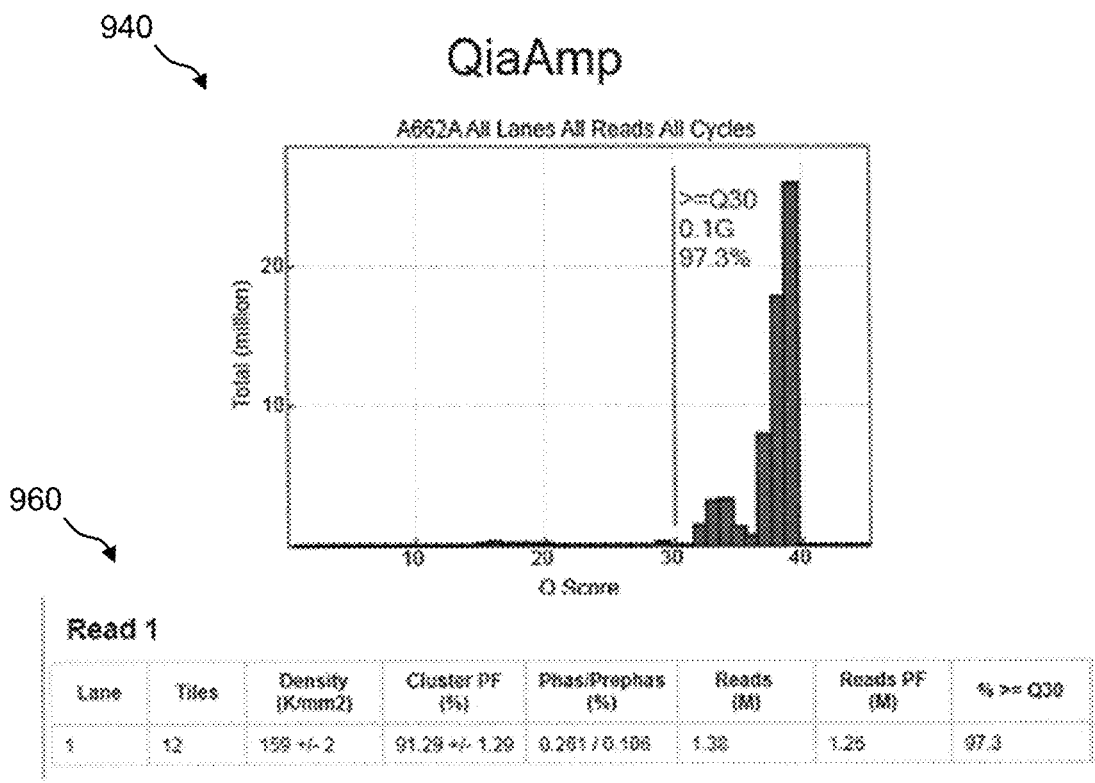
FIG. 9B shows a bar graph of the Q score metric and a data table of sequencing metrics for amplicons generated from DNA prepared from a colon tumor FFPE sample using a QiaAmp DNA purification kit.

FIG. 9A shows a bar graph 900 of the Q score metric and a data table 920 of sequencing metrics for amplicons generated from DNA prepared from a colon tumor FFPE sample according to method 800 of FIG. 8. FIG. 9B shows a bar graph 940 of the Q score metric and a data table 960 of sequencing metrics for amplicons generated from DNA prepared from a colon tumor FFPE sample using a traditional QiaAmp DNA purification kit.

Figures 10A, 10B:
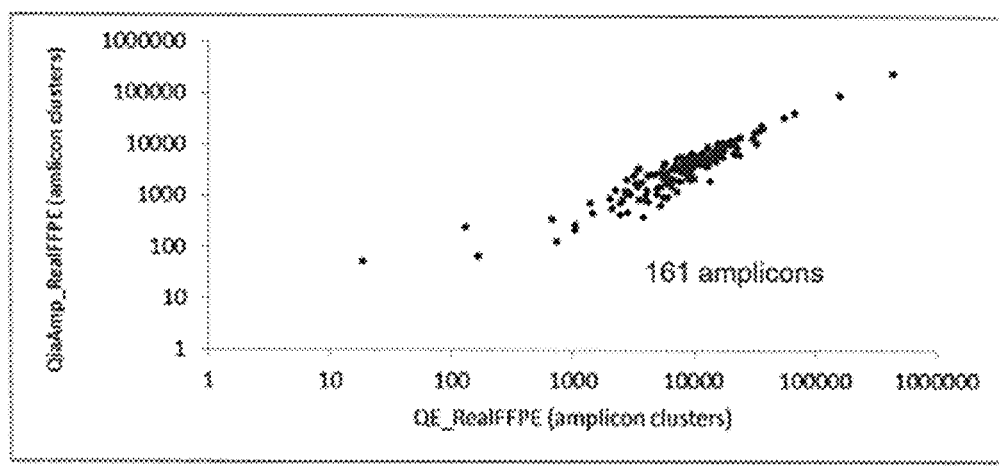
FIGS. 10A and 10B show a data table of sequencing metrics and a plot of amplicon clusters for the QiaAmp prepared DNA and the QuickExtract prepared DNA of FIGS. 9A and 9B.

FIGS. 10A and 10B show a data table 1000 of sequencing metrics and a plot 1050 of amplicon clusters for the QiaAmp prepared DNA and the QuickExtract prepared DNA of FIGS. 9A and 9B. In this sequencing example of the quick extract method, the cluster density is 305,000 clusters per mm$^2$ of flow cell surface, 97% of the clusters pass filters, 97.9% of the passing filters clusters align to the human genome, and 98.7% of the passing filters clusters have a quality of greater or equal to Q30.

As can be seen in FIGS. 9 and 10, in accordance with the methods of the present invention which do not employ DNA purification prior to amplification the results are closely comparable to the more classic method of purifying DNA prior to amplification. Thus, it appears that the methods of the present invention are beneficial in providing comparable results in quicker time and a lower cost than traditional purification methods.

In another example, the extraction of DNA from an FFPE sample and targeted amplification may be combined in a single reaction tube. For example, following the method described above in relation to FIG. 8, the proteinase K in the QuickExtract buffer is first heat inactivated and then combined with targeted DNA amplification mix in a 40:60 ratio. A Horizon FFPE slice is added to this buffer and incubated for 1 hour at 56° C. followed by 2 minutes at 98° C. The sample is then amplified by thermocycling. The data is shown in Table 3. In this sequencing example, the cluster density is 941,000 clusters per mm$^2$ of flow cell surface, 93.6% of the clusters pass filters, 99.5% of the passing filters clusters align to the human genome, and 97.8% of the passing filters clusters have a quality of greater or equal to Q30.

TABLE 3

| MiSeq metrics | |
|---|---|
| Density | 941 K/mm$^2$ |
| PF | 93.6% |
| Align | 99.5% |
| >=Q30 | 97.8% |
| uniformity | 96.3% |

In another example, a Horizon FFPE slice is added to the targeted DNA amplification PCR mix followed directly by thermocycling (optionally no incubation). The data is shown in Table 4. In this sequencing example, the cluster density is 772,000 clusters per mm$^2$ of flow cell surface, 94.4% of the clusters pass filters, 99.4% of the passing filters clusters align to the human genome, and 98% of the passing filters clusters have a quality of greater or equal to Q30.

TABLE 4

| MiSeq metrics | |
|---|---|
| Density | 772 K/mm$^2$ |
| PF | 94.4% |
| Align | 99.4% |
| >=Q30 | 98% |
| uniformity | 91.3% |

Figure 11A:
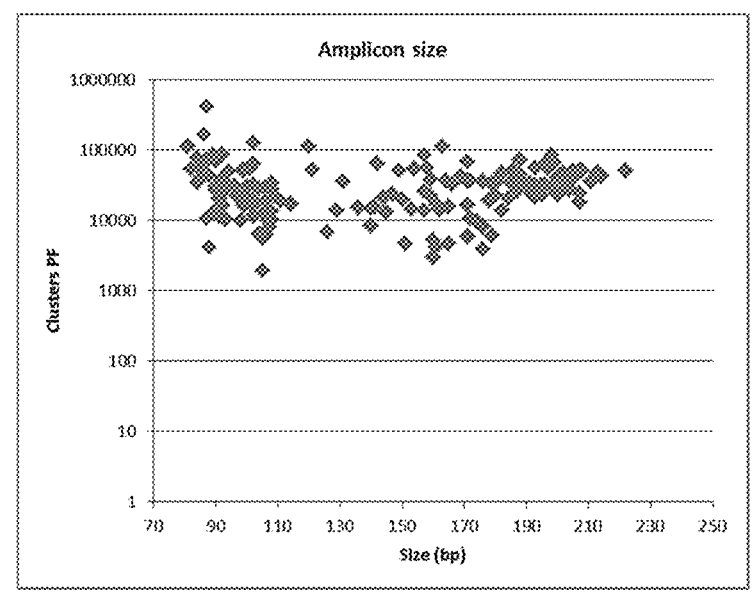
FIGS. 11A and 11B show a plot of amplicon size and a plot of percent GC content, respectively, from the direct targeted amplification of an FFPE slice (no incubation)
Figure 11B:
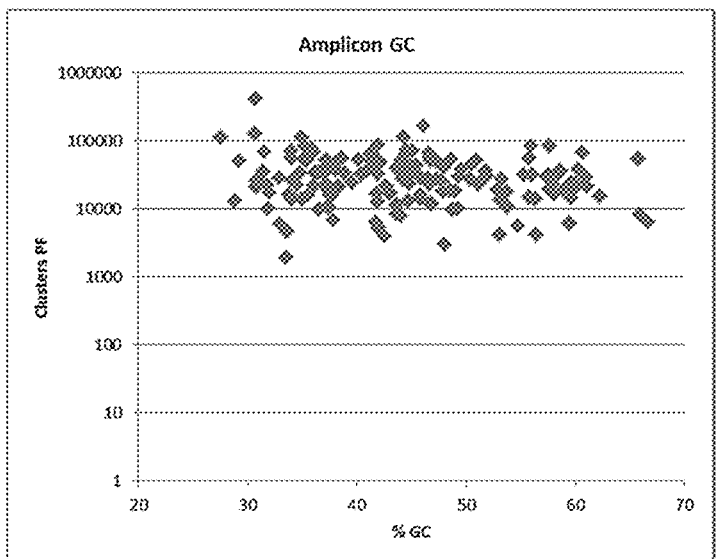

FIGS. 11A and 11B show a plot 1100 of amplicon size and a plot 1150 of percent GC content, respectively, from the direct targeted amplification of an FFPE slice (no incubation). Each point on plots 1100 and 1150 represent an amplicon.

These results are again comparable to more traditional methods involving DNA purification.

Optionally, the present invention can also include the step of sequencing the DNA sequence after amplification. This is preferably conducted via high throughput sequencing methods.

Figure 25:
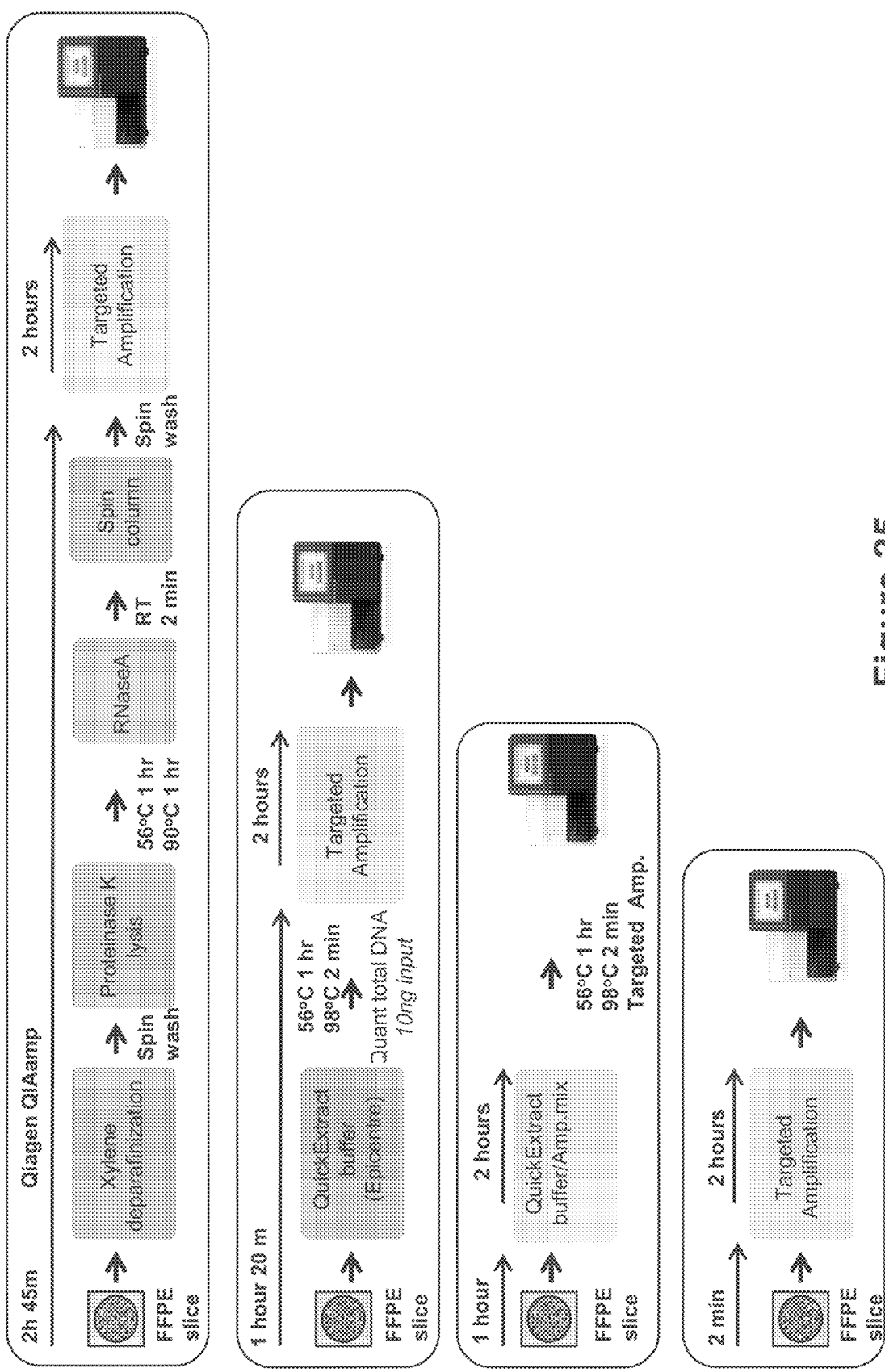
FIG. 25 shows sample preparation workflows for preparing a DNA library from an FFPE sample using modifications of the workflow set forth in FIG. 8.
Figure 27:
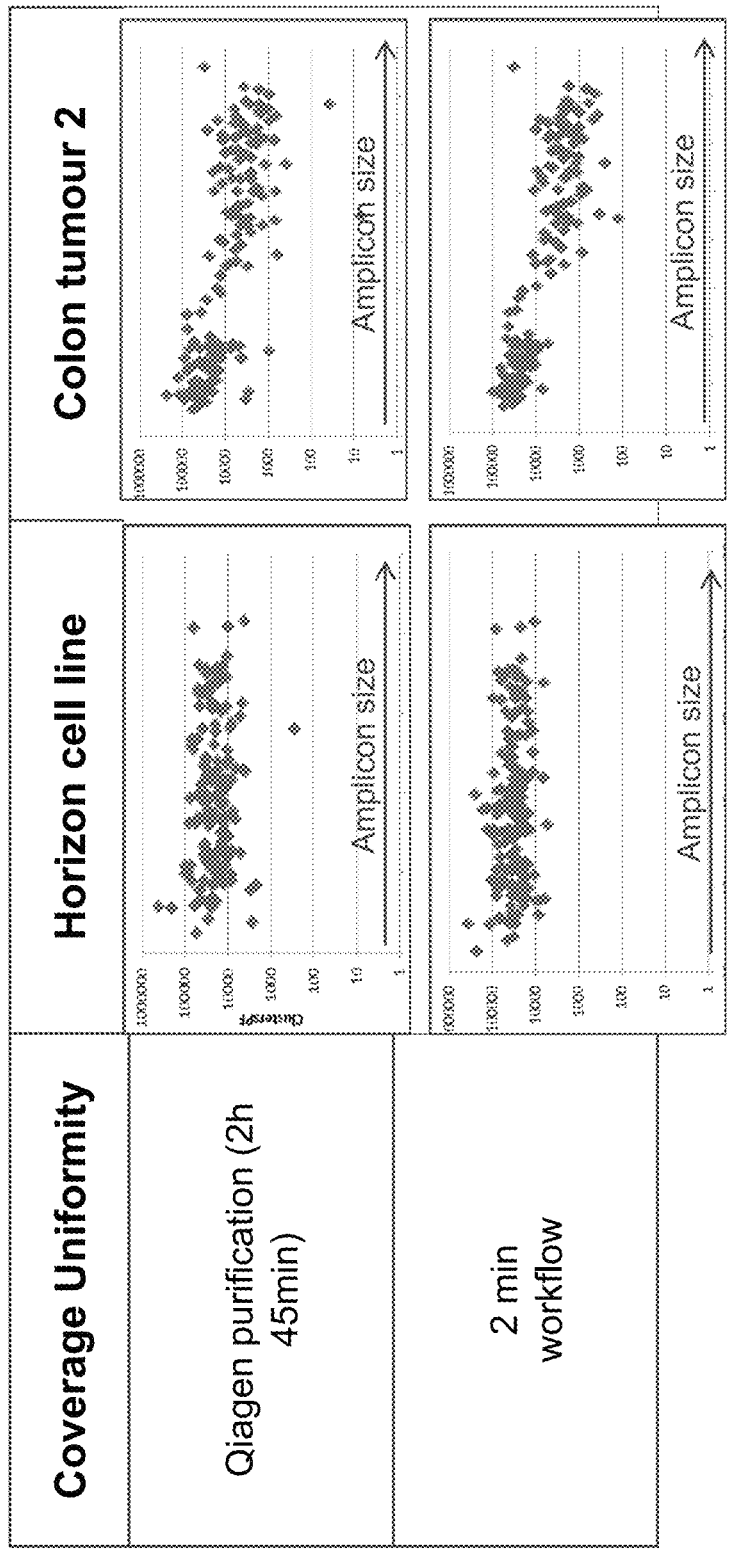
FIG. 27 shows plots of clusters that pass filter for amplicons generated by targeted DNA amplification of FFPE samples prepared according to two methods of FIG. 25.

In some embodiments, as illustrated in FIG. 25, a sequencing library can be prepared directly from an FFPE sample. FIG. 25 shows sample preparation workflows for preparing a DNA library from an FFPE sample using modifications of the workflow set forth in FIG. 8. Typical methods using QIAamp tools rely on a xylene deparafinization step, followed by incubation with proteinase K and heating to remove crosslinking. In FIGS. 26-27, such embodiments are referred to as "Qiagen purification". Typical methods using xylene deparafinization and proteinase K lysis can require close to 3 hours of processing, as indicated in FIGS. 25-27 ("2 h 45 m").

The methods presented herein provide sequencing-ready libraries with minimal handling, thus reducing processing time and removing opportunities for user error and sample loss.

In some embodiments, a sequencing library is prepared by incubating an FFPE sample with an extraction buffer, such as, for example QuickExtract buffer (Epicentre) or another suitable extraction buffer. One suitable buffer is set forth in Table 5 below.

TABLE 5

| Tris HCL pH 7.5 | 50 mM |
|---|---|
| EDTA | 1 mM |
| Proteinase K 100 mg/ml | 0.5 mg/ml |
| 10% Triton X100 | 0.5% |

In some embodiments, as indicated in FIG. 25, an FFPE sample is incubated in an extraction buffer, such as a buffer comprising the components in Table 5. In some embodiments, following an extraction step, total DNA is quantified, and a portion of the extracted DNA is used as input for a targeted amplification reaction, such as PCR amplification as described hereinabove. In FIGS. 26-27, such embodiments are referred to as "1 h 20 min workflow".

Thus, in embodiments presented herein, DNA obtained from FFPE is subjected to targeted amplification, and the amplicons generated are sequenced by, for example, SBS methodology. In some such embodiments, because DNA obtained from FFPE is not purified prior to placing on a sequencing instrument, the sequencing apparatus (flowcells and the like) will comprise components from the FFPE sample besides DNA. Examples of FFPE components include, for example, formalin, paraffin, cellular components, protein, extracellular matrix components, collagen, tissue debris, and the like.

Thus, presented herein is a method of performing a clustering reaction on a solid surface, wherein the clustering reaction is performed in the presence of one or more of formalin, paraffin, cellular components, protein, extracellular matrix components, collagen, and tissue debris. In some embodiments, the clustering reaction is performed in the presence of at least 0.001 pg paraffin. In some embodiments, the clustering reaction is performed in the presence of at least 0.01 pg, 0.1 pg, 1 pg, 10 pg, 100 pg, 1 ng, 10 ng, 100 ng, 1 μg, 10 μg, 100 μg, or at least 1 mg paraffin.

Presented herein is a flowcell comprising immobilized amplification primers and one or more of formalin, paraffin, cellular components, protein, extracellular matrix components, collagen, and tissue debris. In some embodiments, the flowcell comprises at least 0.001 pg paraffin. In some embodiments, the flowcell comprises at least 0.01 pg, 0.1 pg, 1 pg, 10 pg, 100 pg, 1 ng, 10 ng, 100 ng, 1 µg, 10 µg, 100 µg, or at least 1 mg paraffin.

Thus, presented herein is a method of performing a clustering reaction on a solid surface, wherein the clustering reaction is performed in the presence of proteinase K. In some embodiments, the clustering reaction is performed in the presence of at least 0.001 pg proteinase K. In some embodiments, the clustering reaction is performed in the presence of at least 0.01 pg, 0.1 pg, 1 pg, 10 pg, 100 pg, 1 ng, 10 ng, 100 ng, 1 µg, 10 µg, 100 µg, or at least 1 mg proteinase K.

Presented herein is a flowcell comprising immobilized amplification primers and proteinase K. In some embodiments, the flowcell comprises at least 0.001 pg proteinase K. In some embodiments, the flowcell comprises at least 0.01 pg, 0.1 pg, 1 pg, 10 pg, 100 pg, 1 ng, 10 ng, 100 ng, 1 µg, 10 µg, 100 µg, or at least 1 mg proteinase K.

In some embodiments, as indicated in FIG. 25, PCR amplification is performed without performing DNA quantification. In FIGS. 26-27, such embodiments are referred to as "lh 2 min workflow".

In all embodiments depicted in FIG. 25, an aliquot of the amplification reaction was placed directly into a MiSeq flowcell and clustering, followed by SBS sequencing, was performed according to manufacturer instructions.

In typical embodiments, an FFPE slice is about 10 µm in thickness. In some embodiments, an FFPE slice can be as thin as around 1, 2, 3, 4, 5, 6, 7, 8, 9 or more than 9 µm in thickness. Thus, in a 10 µm thick FFPE slice, paraffin ranging from 0.1, 0.5, 1, 2, 3, 4, 5, 6, 7, 8, 9, 10, 11, 12, 13, 14, 15, 16, 17, 18, 19, 20 or more than 20 mg of paraffin can be present. Similarly, in a 10 µm thick FFPE slice, tissue ranging from 0.1, 0.5, 1, 2, 3, 4, 5, 6, 7, 8, 9, 10, 11, 12, 13, 14, 15, 16, 17, 18, 19, 20 or more than 20 mg of tissue can be present. These components are transferred into a sequencing flowcell in embodiments presented herein. In some embodiments, a tissue slice is contacted with 10, 20, 30, 40, 50, 60, 70, 80, 90, 100 or more than 100 µL of an extraction buffer comprising a proteinase, such as proteinase K. On typical extraction buffer is set forth above in Table 5.

In some embodiments, as indicated in FIG. 25, an FFPE sample placed directly into an amplification reaction, such as PCR amplification buffer, without first performing a separate extraction step. In FIGS. 26-27, such embodiments are referred to as "2 min workflow".

FIG. 26 is a data table comparing coverage uniformity obtained for sequencing libraries obtained using 4 different workflows from 3 different FFPE samples. Surprisingly, clustering and sequencing performed in the presence of one or more of proteinase K, formalin, paraffin, cellular components, protein, extracellular matrix components, collagen, and tissue debris resulted in sequencing coverage uniformity which is comparable to those obtained using purified DNA.

FIG. 27 shows plots of clusters that pass filter for amplicons generated by targeted DNA amplification of FFPE samples prepared according to two methods of FIG. 25. Surprisingly, clustering and sequencing performed in the presence of one or more of proteinase K, formalin, paraffin, cellular components, protein, extracellular matrix components, collagen, and tissue debris resulted in sequencing coverage uniformity which is comparable to those obtained using purified DNA.

Sequencing Directly from Dried Blood Spots

Figure 12:
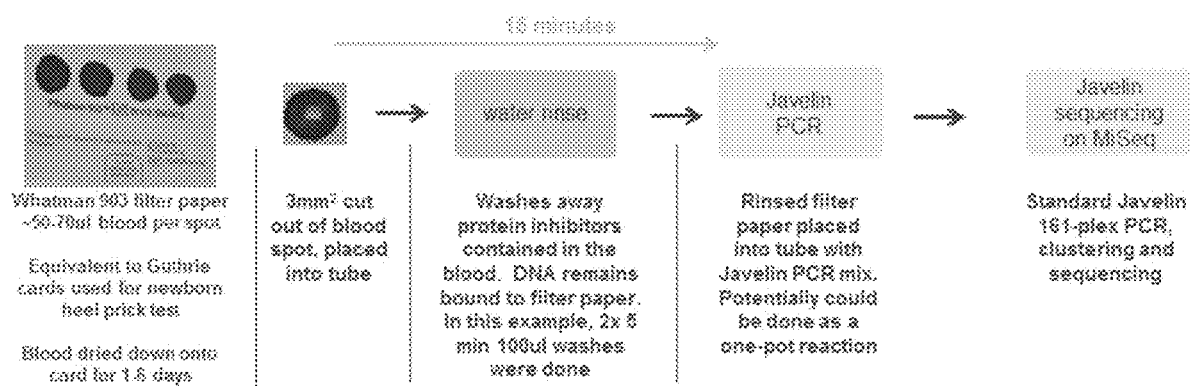
FIG. 12 illustrates an example of a method of sequencing from dried blood spots.

The inventors have also shown that amplicon sequencing can be carried out directly from dried blood spots. In this experiment, shown in FIG. 12, dried blood spots where provided on Whatman 903 filter paper with ~50-70 ul blood per spot. This is equivalent to the dried blood spots found on Guthrie cards used for newborn heel prick tests. In this experiment blood was dried down onto the paper for 1-6 days.

Figures 13A, 13B:
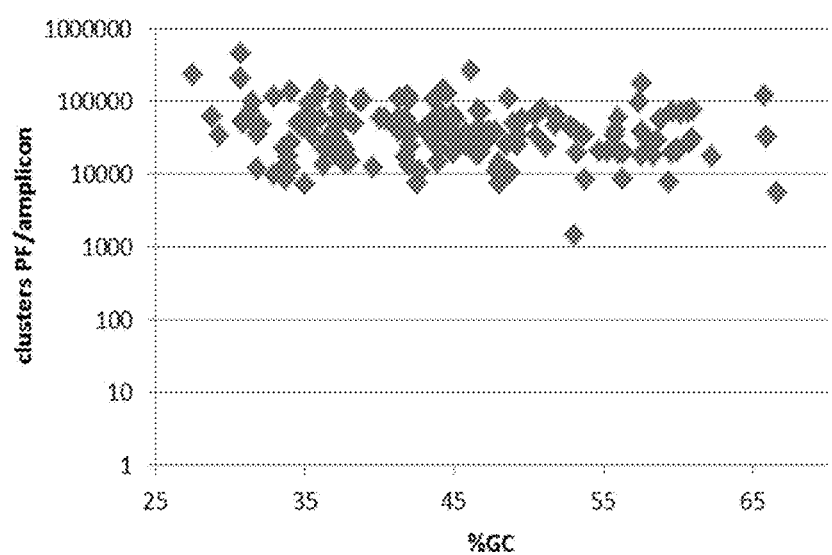
FIGS. 13A (a data table of sequencing metrics) and 13B (a plot of amplicon size and a plot of percent GC content) show the results of the sequencing of FIG. 12.

A 3 $mm^2$ portion was cut out from the blood spot and placed into a tube. The portion is rinsed with water which washes away protein inhibitors contained in the blood. DNA remains bound to filter paper. In this example, 2×5 min 100 ul washes were carried out. Rinsed filter paper placed into tube with PCR mix. Potentially this could be done as a one-pot reaction. PCR, clustering and sequencing is then carried out. Results can be seen in FIGS. 13A and 13B.

Figure 14:
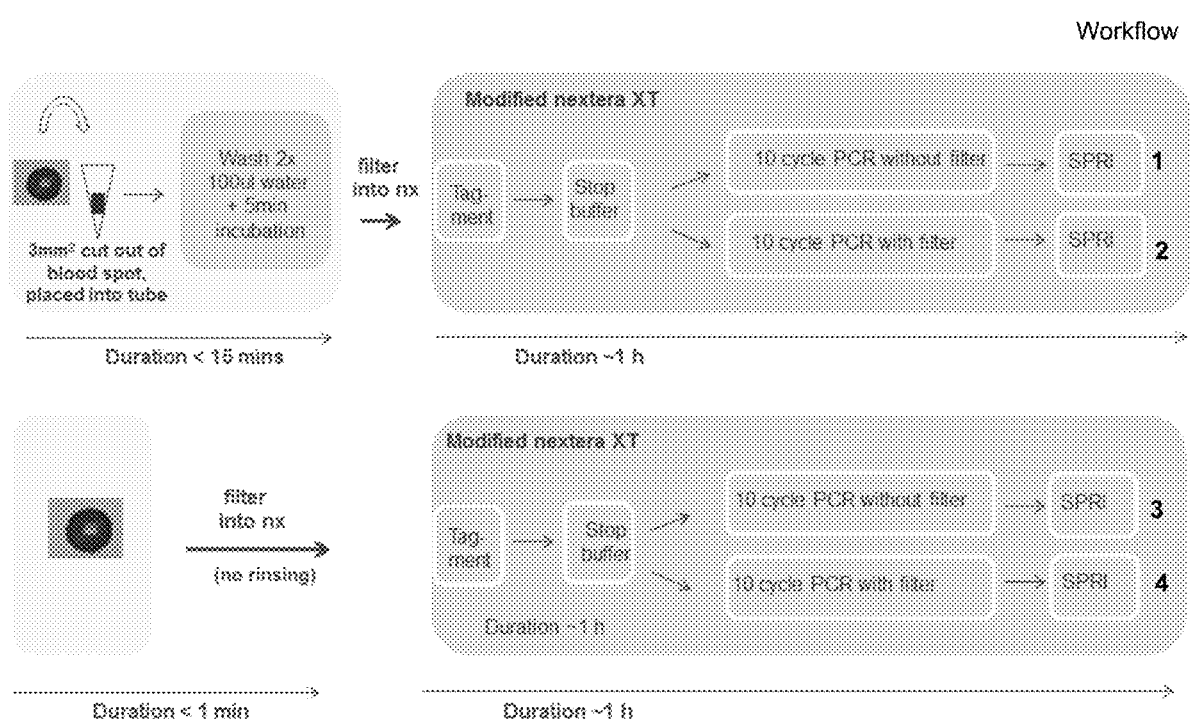
FIG. 14 illustrates an example of a method of tagmentation and sequencing from blood spots with the upper panel including a wash step in water and the lower panel omitting the wash step in water.

Experiments were also carried out to show that tagmentation based whole genome sequencing can be carried out on dried blood spots. FIG. 14 shows the experiment carried out both with a water wash step (top) and without (bottom). Again 3 $mm^2$ portions were cut out from the blood spot and placed into a tube. In the top panel the portion is washed twice with water and incubated for 5 minutes. In the bottom panel no wash step occurs. In both cases tagmentation, PCR (with and without filter) and sequencing then occurs with the results being shown in FIG. 15.

Bead Based Nextera (BBN)

Methods for performing bead based tagmentation, also referred to herein as bead based Nextera™ (BBN) are described in the materials of U.S. Application Ser. No. 62/167,463, filed May 28, 2015, the content of which is incorporated by reference in its entirety. Briefly, as performed in some embodiments presented herein, BBN can be performed as follows. 20 µL of blood sample is mixed with 20 µL of magnetic beads (100 nM TSM) and 10 ul of tagment buffer (TD) and incubated for 15 min at 55° C. 12.5 µL of NT buffer is added to the sample and incubated for 5 min at room temperature. The sample is placed on a magnet, supernatant removed. The beads were washed three times with 100 µL of HT2 buffer for each wash step. The sample is PCR amplified using 5 µL of both index primers (e.g., indexes N702 and N507), 15 µL Nextera PCR mastermix (NPM), and 5 µL PCR primer cocktail (PPC). Thermal amplification is performed according to manufacturer's recommendation ((e.g. 5 PCR cycles). The tube containing the beads and sample is placed on magnet and supernatant purified using ZYMO columns (Zymo Research) and SPRI beads.

Figure 16:
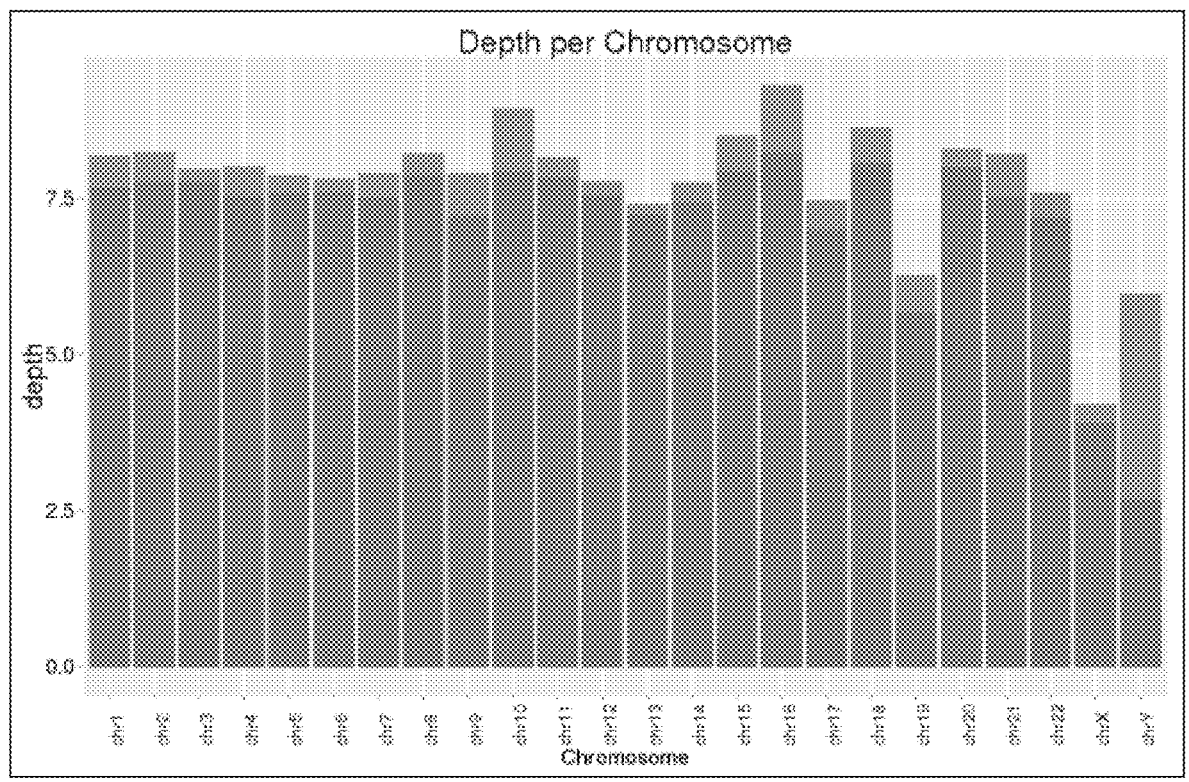
FIG. 16 shows a data table of sequencing metrics (top) and a graph showing sequencing depth per chromosome (bottom) for a sample preparation method of preparing a whole blood sample for construction of a tagmented DNA library (Nextera) performed according to the workflow illustrated in FIG. 6.
Figure 17:
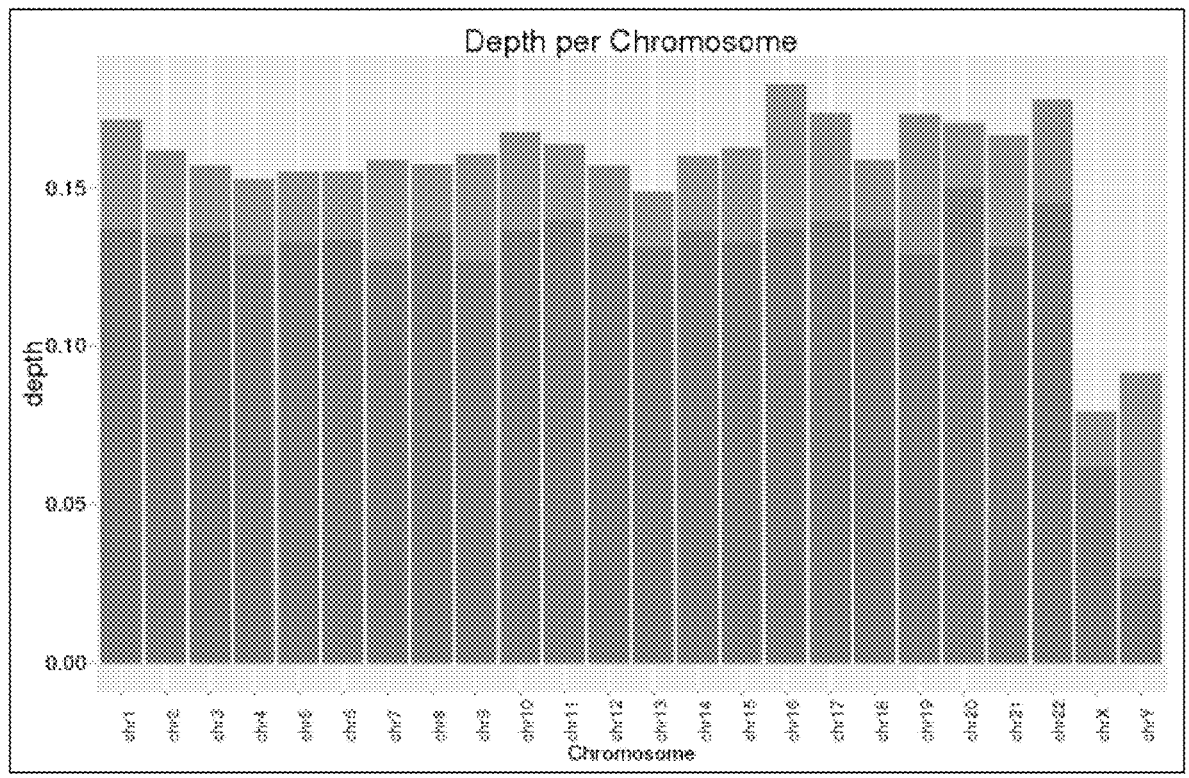
FIG. 17 shows a data table of sequencing metrics (top) and a graph showing sequencing depth per chromosome (bottom) for a sample preparation method of preparing a whole blood sample for construction of a tagmented DNA library (Nextera) performed according to the workflow illustrated in FIG. 6, but using bead-based tagmentation for the tagmentation step.
Figure 18:
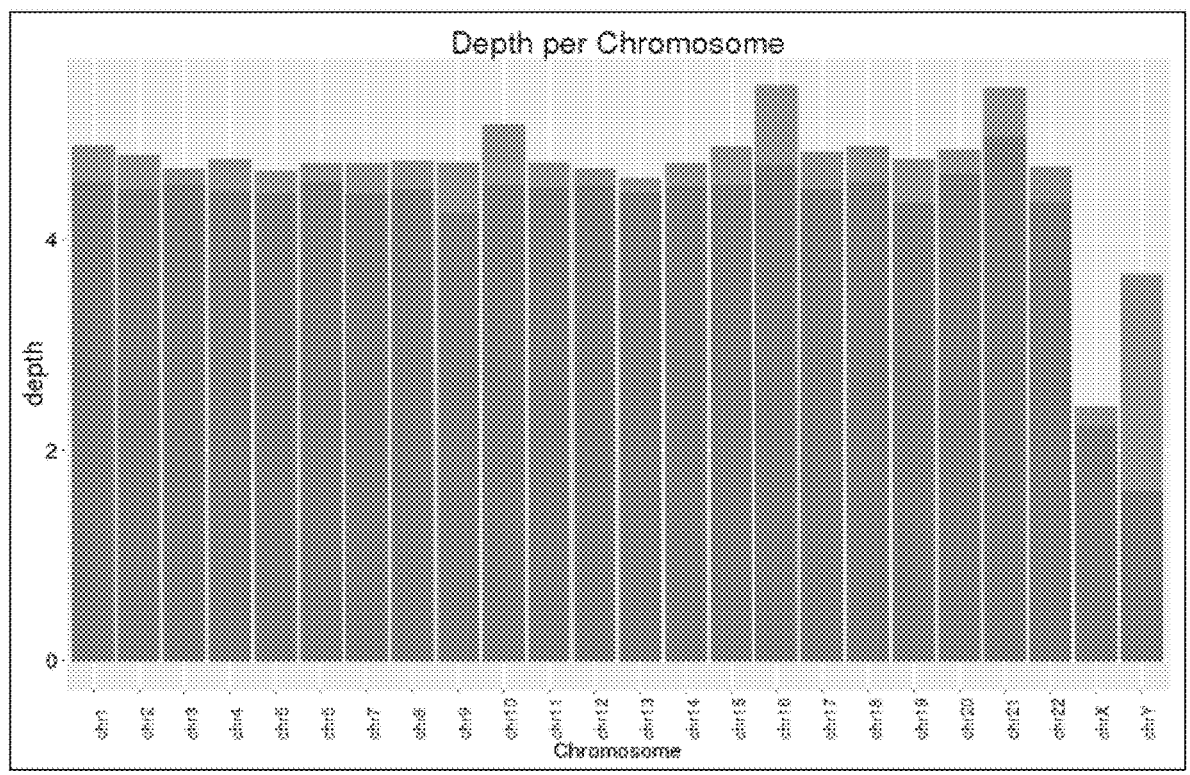
FIG. 18 shows a data table of sequencing metrics (top) and a graph showing sequencing depth per chromosome (bottom) for a sample preparation method of preparing a tagmented DNA library (Nextera) performed by rinsing a dried blood spot in water, followed by tagmentation (Nextera).

A comparison of Bead Based Nextera with other whole blood library preparation methods was performed. FIGS. 16, 17 and 18 show sequencing metrics and sequencing depth per chromosome of a tagmented DNA library prepared according to three different methods. For the data shown in FIG. 16, a library from whole blood was prepared generally according to method 600 of FIG. 6. In particular, 2 µL whole blood was mixed with 12 µL water and then incubated with proteinase K at 56° C. for 10 minutes. Tagmentation reagents were then added to the lysate and tagmentation performed as described above. An aliquot of the tagmented DNA library was loaded onto a flow cell for clonal amplification (cluster generation) and sequencing (MiSeq). For the data shown in FIG. 17, a modification of the above protocol was made. Specifically, cellular debris was pelleted after lysis with water, and prior to incubation with proteinase K. After proteinase K incubation, the sample was centrifuged to remove solid debris, and then bead based Nextera was performed as described above. For the data shown in FIG. 18, a 3 mm² piece of filter paper having a dried blood spot was rinsed with water for 15 minutes, and the solubilized DNA was removed and tagmentation performed as described above.

The sequencing metrics are shown in Tables for the 3 methods respectively in FIGS. 16, 17 and 18. In this sequencing example, the cluster densities are 4.11 billion, 2.25 billion and 0.85 billion clusters per mm² of flow cell surface for the three workflows respectively. GC and AT drop out are also given in the tables for the three methods, respectively.

Figure 20:
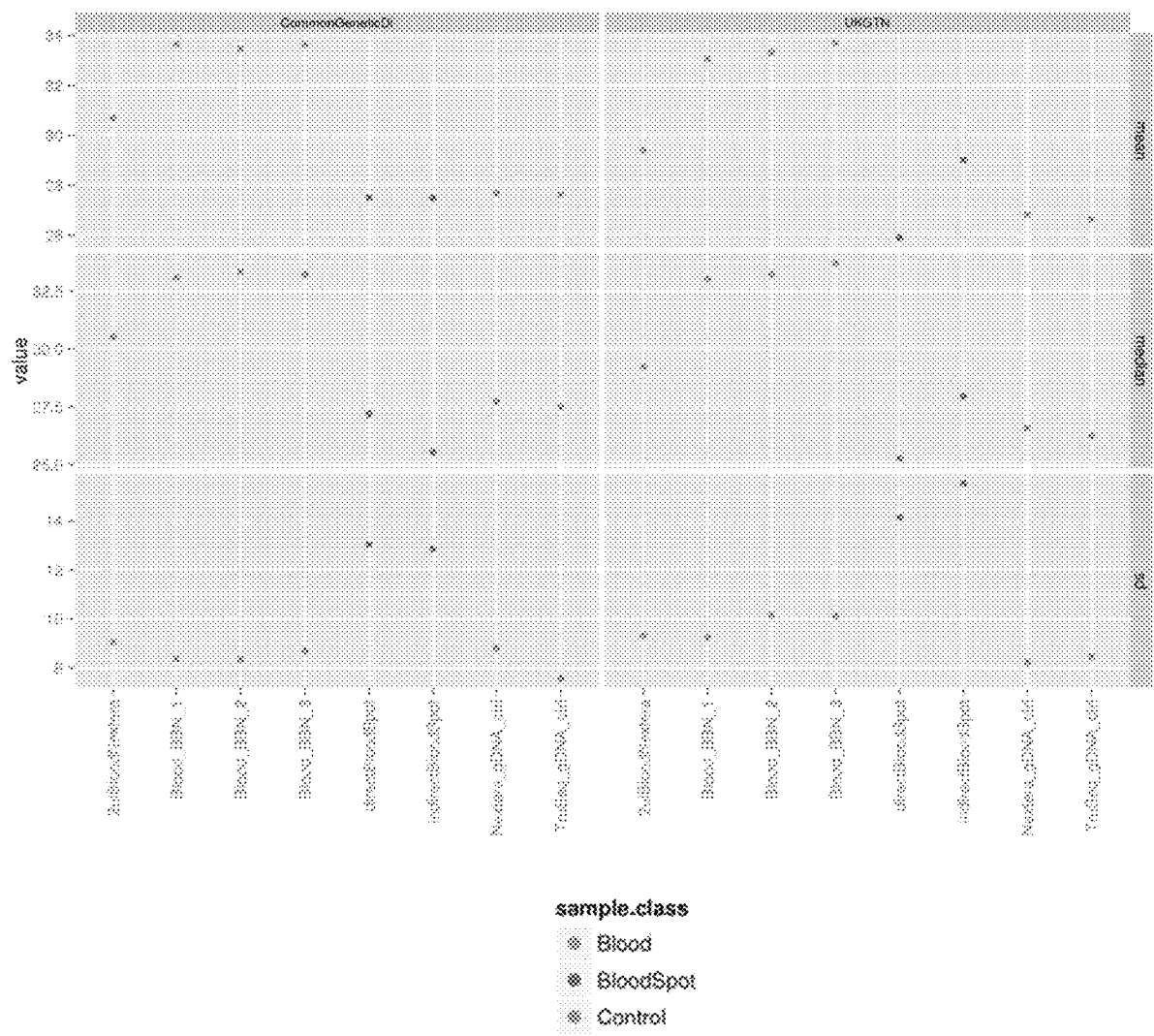
FIG. 20 is a graph showing coverage for gene panels of interest from Common Genetic Disorders and UK Genetic testing network (UKGTN) for blood samples sequenced using BBN, dried blood spots, and control gDNA. Shown are median values (top two panels) and standard deviation (lower panel).
Figure 21:
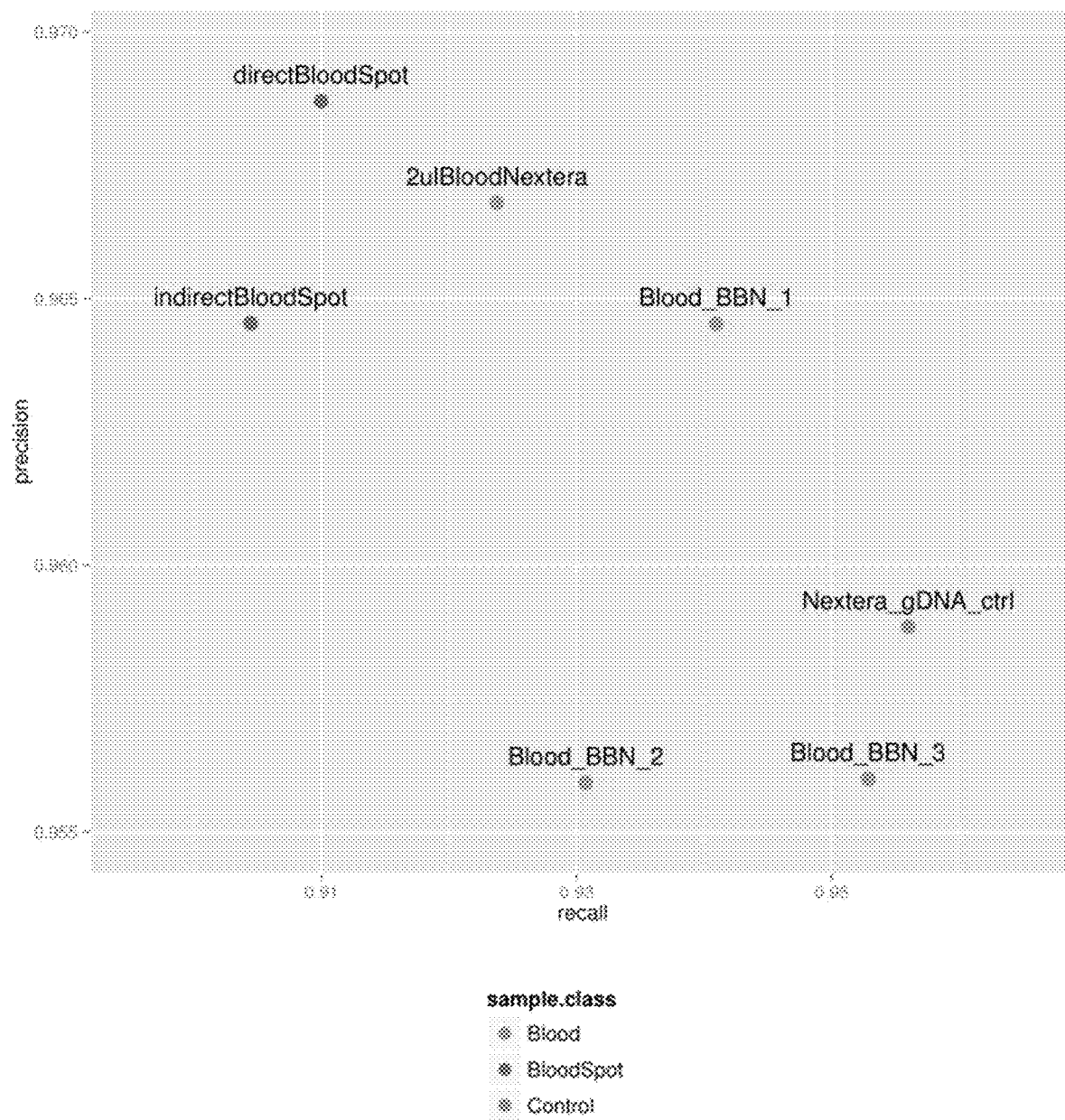
FIG. 21 is a graph comparing precision and recall for SNP concordance for blood samples sequenced using BBN, dried blood spots, and control gDNA.

FIG. 19 shows a comparison of the sequencing metrics for three BBN samples (BBN1, 2, 3) as compared to sequencing metrics of purified gDNA controls and dried blood spots, prepared as described above. In this sequencing example, the cluster density, % of the clusters passing filters, % of the passing filters clusters align to the human genome, and % of the passing filters clusters having a quality of greater or equal to Q30 are comparable for BBN samples, dried blood, and purified gDNA samples. FIGS. 20 and 21 show additional comparisons of coverage of gene panels of interest (FIG. 20) and genotype precision and recall related to SNP concordance (FIG. 21), indicating that data output for the three methods are comparable.

Non-Tagmented Libraries

Figure 22:
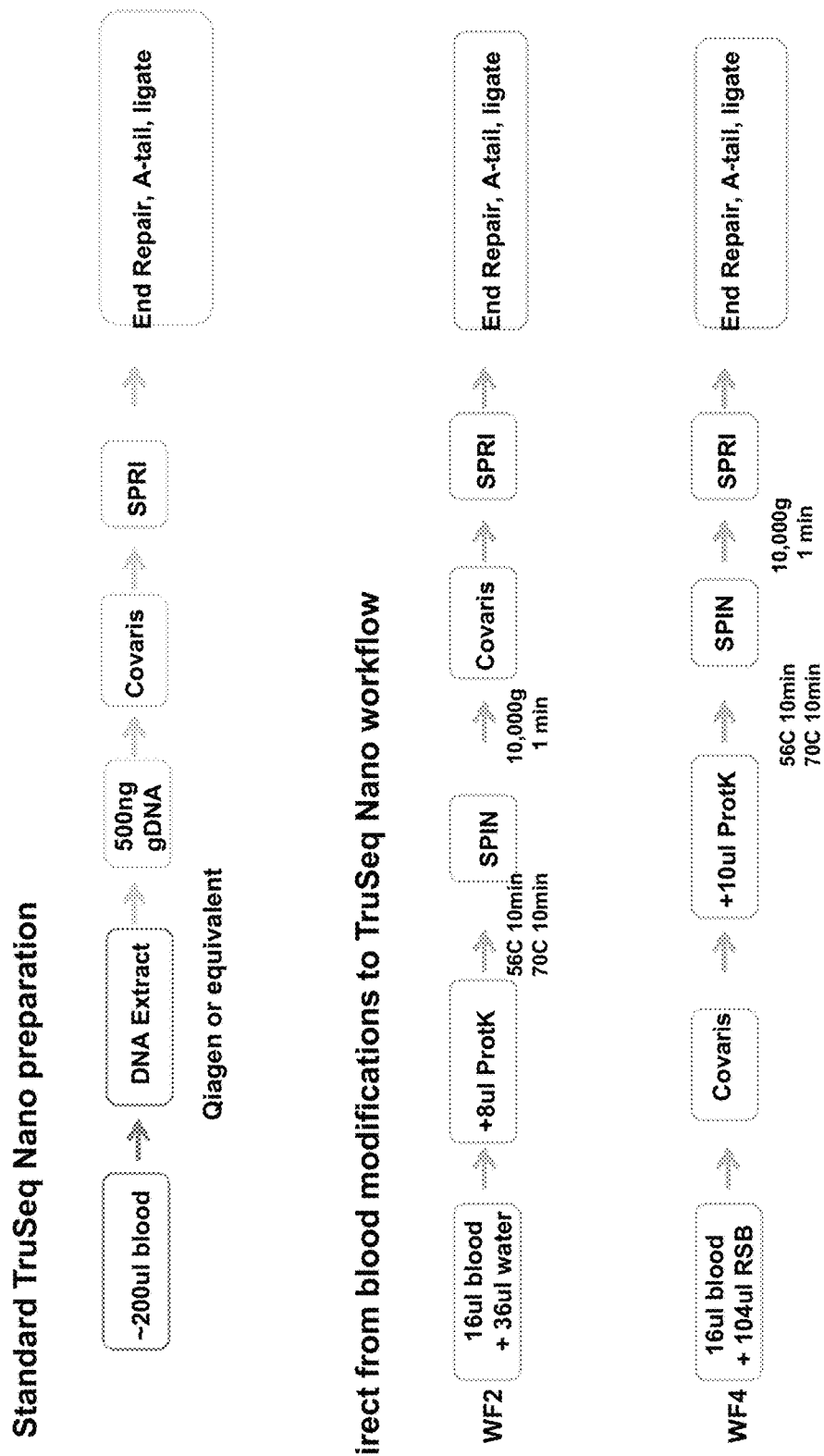
FIG. 22 shows sample preparation workflows for preparing a DNA library from a whole blood sample using standard TruSeq Nano method or modifications thereof.

In some embodiments presented herein, a method for library preparation from whole blood can involve adapter ligation, thus avoiding the need for tagmentation reagents. As shown in FIG. 22, a standard library preparation method, designated as "TruSeq Nano" includes DNA extraction, shearing (Covaris), cleanup and size selection (SPRI), followed by end repair, A-tailing and adapter ligation. It has been surprisingly discovered that modifications to this workflow can greatly improve library preparation from whole blood samples, as demonstrated by several metrics.

In one embodiment, library preparation directly from blood using modifications to the Illumina TruSeq Nano kit is described. Briefly, as illustrated by WF-2 in FIG. 22, 16 µl of blood was mixed with 36 µL water and 8 µL of Proteinase K and incubated at 56° C. for 10 min followed by 70° C. for 10 min. Samples were spun down at 10,000 g for 1 min followed by shearing using Covaris sonication. The sample was then purified using SPRI beads and followed by end repair, A-tailing, ligation and PCR amplification according to manufacturer recommendations for TruSeq Nano (Illumina, Inc). In another embodiment, illustrated in FIG. 22 as workflow (WF-4), 16 µl of blood is mixed with 104 µL RSB (10 mM Tris pH 7.0) followed by shearing on COVARIS. 8 µL of Proteinase K was added to the sheared blood sample and incubated at 56° C. for 10 min followed by 70° C. for 10 min. Samples were spun down at 10,000 g for 1 min. Sample was purified using SPRI beads and followed by end repair, A-tailing, ligation and PCR amplification according to manufacturer recommendations for TruSeq Nano (Illumina, Inc).

Figure 23:
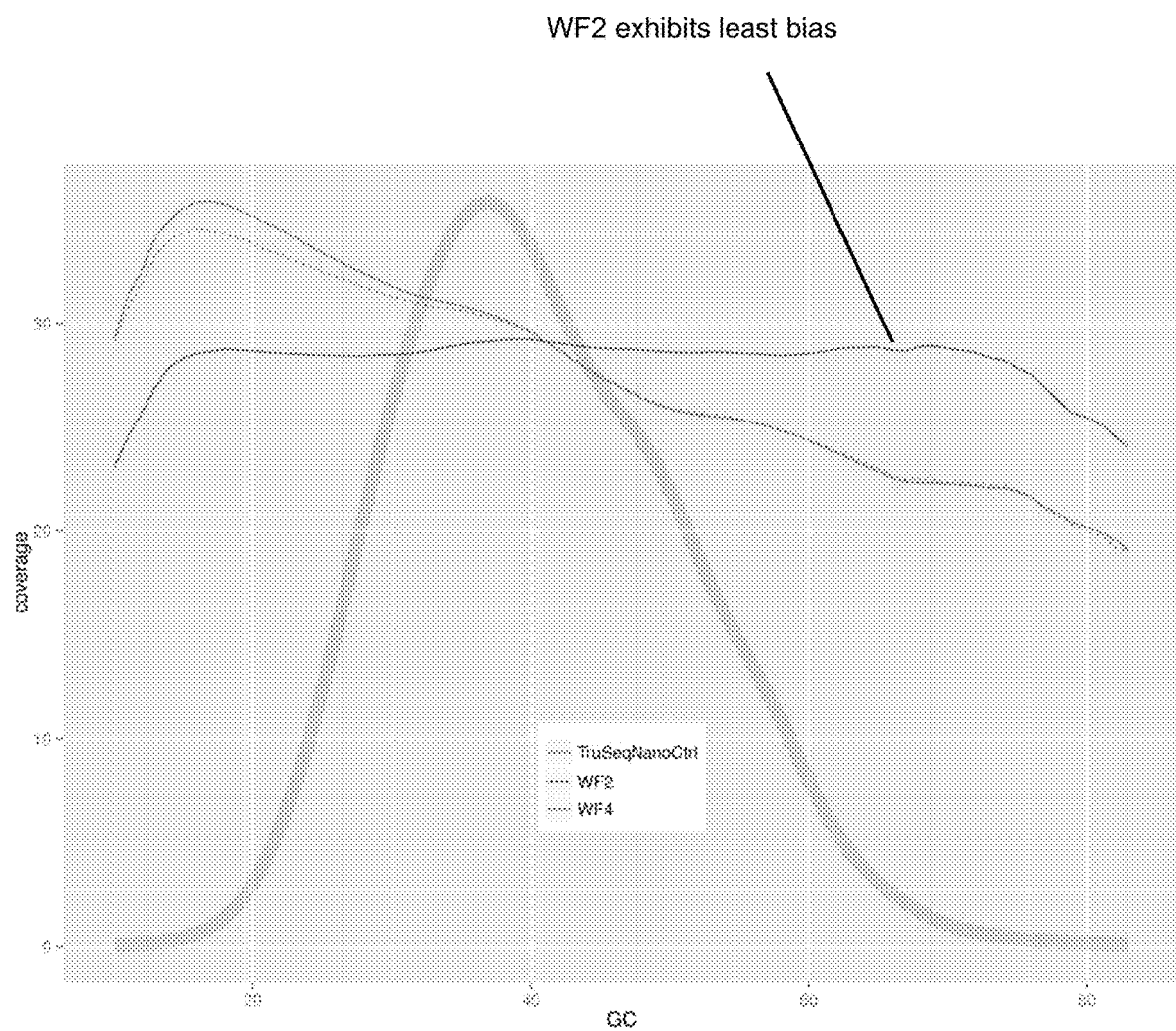
FIG. 23 is a graph showing GC bias profile of libraries prepared according to the workflows illustrated in FIG. 22.

FIG. 23 shows the GC bias profiles of libraries prepared from the three TrueSeq Nano workflows described above for whole blood. As shown in FIG. 23, WF2 exhibited a better GC bias profile, representing an unexpected finding and a significant improvement over the control DNA sample preparation.

Figure 24:
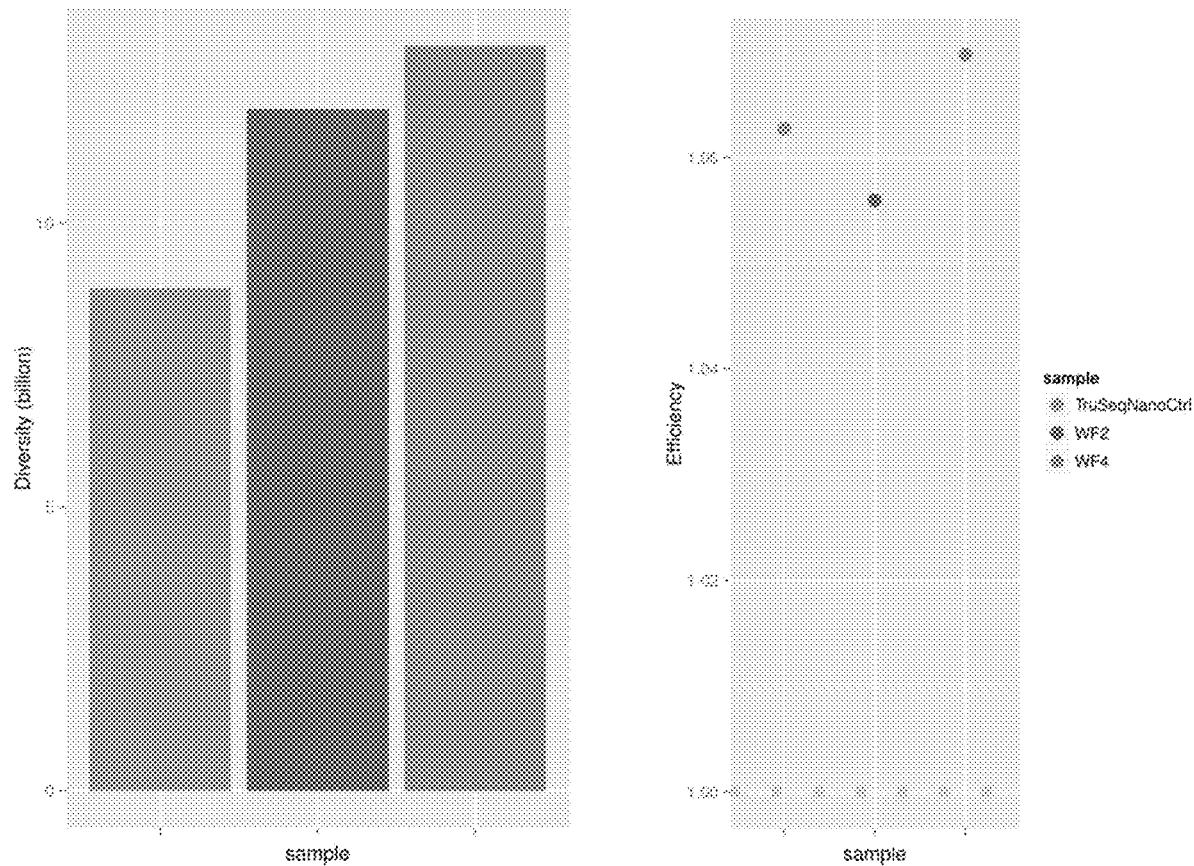
FIG. 24 shows graphs comparing library diversity (left panel) and sequencing efficiency (right panel) of libraries prepared according to the workflows illustrated in FIG. 22.

FIG. 24 shows that the diversity of WF-2 and WF-4 are higher than that of control sample.

In summary, Workflows 2 and 4 (WF-2, WF-4) resulted in overall better coverage and callability. Both workflows avoid the need for DNA extraction, offering significant savings in cost and time.

Sequencing Methods

In principle, next generation sequencing (NGS) is similar to Sanger-based, or CE sequencing. The bases of a small fragment of DNA are sequentially identified from signals emitted as each fragment is re-synthesized from a DNA template strand. NGS extends this process across millions of reactions in a massively parallel fashion, rather than being limited to a single or a few DNA fragments. This advance enables rapid sequencing of large stretches of DNA, with the latest instruments capable of producing hundreds of gigabases of data in a single sequencing run. To illustrate how this process works, consider a single genomic DNA (gDNA) sample. The gDNA is first fragmented into a library of small segments and sequenced. The newly identified strings of bases, called reads, are then reassembled using a known reference genome as a scaffold (resequencing), or assembled together using advanced computational techniques if no reference genome is available (de novo sequencing). The full set of aligned reads reveals the entire genomic sequence of the sample. Once the sample library is prepared, all of the sequencing steps through data analysis can be performed on a single instrument, facilitating rapid turnaround with minimal hands-on time.

With NGS, researchers can start directly from a gDNA or cDNA library. The DNA fragments are then ligated to specific oligonucleotide adapters needed to perform the sequencing biochemistry, requiring as little as 90 minutes with Illumina's Nextera® technology. In contrast, CE-based Sanger sequencing requires genomic DNA to be fragmented first and cloned into either bacterial artificial chromosomes (BACs) or yeast artificial chromosomes (YACs). Then, each BAC/YAC must be further subcloned into a sequencing vector and transformed into the appropriate microbial host. Template DNA is then purified from individual colonies or plaques prior to sequencing. This process can take days or even weeks to complete.

Sequencing by Synthesis (SBS) Technology

Illumina's sequencing instruments and reagents support massively parallel sequencing using a proprietary method that detects single bases as they are incorporated into growing DNA strands.

SBS Chemistry

A fluorescently labeled reversible terminator is imaged as each dNTP is added, and then cleaved to allow incorporation of the next base. Since all four reversible terminator-bound dNTPs are present during each sequencing cycle, natural competition minimizes incorporation bias. The end result is true base-by-base sequencing that enables the industry's most accurate data for a broad range of applications.

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, C T, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

Throughout this application various publications, patents and patent applications have been referenced. The disclosures of these publications in their entireties are hereby incorporated by reference in this application in order to more fully describe the state of the art to which this invention pertains.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

What is claimed is:

1. A method of preparing a nucleic acid-containing cellular sample for library amplification comprising the following steps:
  (a) providing a nucleic acid-containing cellular sample, wherein the sample is a blood sample or a formalin-fixed paraffin-embedded (FFPE) sample;
  (b) lysing cells of the sample with a lysis reagent to liberate nucleic acids from within the cells of the cellular sample, thereby forming a lysate comprising liberated nucleic acids; and (c) performing tagmentation on liberated nucleic acids in the lysate without purifying the liberated nucleic acids prior to tagmentation, thereby forming tagmented nucleic acids.

2. The method of claim 1, wherein the nucleic acids are DNA.

3. The method of claim 1, wherein the blood sample is a whole blood sample or a dried blood sample.

4. The method of claim 1, wherein the sample is an FFPE sample.

5. The method of claim 1, wherein the lysis reagent is water, purified water, or distilled water.

6. The method of claim 1, wherein the lysis reagent is a detergent, a base, an acid, and/or an enzyme.

7. The method of claim 1, wherein step (b) comprises treating the cells of the sample or the lysate with an enzyme to disrupt the structure of the nucleic acids.

8. The method of claim 7, wherein the nucleic acids are DNA and the enzyme that disrupts the structure is proteinase K.

9. The method of claim 1, further comprising neutralizing the lysis reagent prior to the tagmentation step (c) to inactivate the lysis reagent.

10. The method of claim 9, wherein neutralizing the lysis reagent is carried out via a neutralizing agent or via heat.

11. The method of claim 1, further comprising incubating the lysate before the tagmentation step.

12. The method of claim 1, wherein the steps of lysing the sample and performing tagmentation on the liberated nucleic acids in the lysate are conducted in a single pot reaction.

13. The method of claim 1, further comprising sequencing the tagmented nucleic acids to ascertain their nucleic acid sequences.

14. The method of claim 13, wherein the sequencing is performed by high-throughput sequencing or a sequence-by-synthesis protocol.

15. The method of claim 1, further comprising:
   (d) exposing the tagmented nucleic acids to a solid surface with immobilized amplification primers, thereby immobilizing the tagmented nucleic acids on the solid surface; and
   (e) clonally amplifying the immobilized, tagmented nucleic acids on the solid surface in a clustering reaction to generate clusters.

16. The method of claim 15, wherein the clustering reaction is performed in the presence of one or more of proteinase K, formalin, paraffin, cellular components, protein, extracellular matrix components, collagen, and tissue debris.

17. The method of claim 16, wherein the clustering reaction is performed in the presence of at least 0.01 pg, 0.1 pg, 1 pg, 10 pg, 100 pg, 1 ng, 10 ng, 100 ng, 1 μg, 10 μg, 100 μg, or at least 1 mg paraffin.

18. The method of claim 16, wherein the sample is an FFPE sample and the clustering reaction is performed in the presence of at least 0.001 pg paraffin.

19. The method of claim 16, wherein the clustering reaction is performed in the presence of at least 0.01 pg, 0.1 pg, 1 pg, 10 pg, 100 pg, 1 ng, 10 ng, 100 ng, 1 μg, 10 μg, 100 μg, or at least 1 mg proteinase K.

20. The method of claim 16, wherein the clustering reaction is performed in the presence of at least 0.001 pg proteinase K.

* * * * *